United States Patent
Marcu et al.

(10) Patent No.: US 6,272,376 B1
(45) Date of Patent: Aug. 7, 2001

(54) TIME-RESOLVED, LASER-INDUCED FLUORESCENCE FOR THE CHARACTERIZATION OF ORGANIC MATERIAL

(75) Inventors: Laura Marcu, So. Pasadena; Warren S. Grundfest, Los Angeles; Jean-Michel I. Maarek, Rancho Palos Verdes, all of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/235,710

(22) Filed: Jan. 22, 1999

(51) Int. Cl.$^7$ .................................................. A61B 6/00
(52) U.S. Cl. ............................................... 600/477
(58) Field of Search ................... 436/164, 514, 436/518; 435/29, 7.2, 7.21, 7.23; 530/350; 600/476, 477

(56) References Cited

U.S. PATENT DOCUMENTS

| | | |
|---|---|---|
| 5,419,323 | 5/1995 | Kittrell et al. . |
| 5,541,081 * | 7/1996 | Hardy et al. ............................ 435/29 |
| 5,660,997 * | 8/1997 | Spaulding ........................... 435/7.21 |
| 5,769,081 | 6/1998 | Alfano et al. . |
| 5,888,829 * | 3/1999 | Gee et al. ............................. 436/164 |

OTHER PUBLICATIONS

O'Brien, et al. "Development and Evaluation of Spectral Classification Algorithms for Fluorescence Guided Laser Angioplasty." *IEEE Transactions on Biomedical Engineering*, vol. 36, No. 4, (Apr. 1989).

Richards–Kortum, et al. "Spectral Diagnosis of Atherosclerosis Using an Optical Fiber Laser Catheter." *American Heart Journal*, vol. 118, No. 2 (Aug. 1989).

Fitzmaurice, et al. "Argon Ion Laser–Excited Autofluorescence in Normal and Atherosclerotic Aorta and Coronary Arteries: Morphologic Studies." *American Heart Journal*, vol. 118, No. 5, Part 1 (Nov. 1989).

Laifer, et al. "Biochemical Basis for the Difference Between Normal and Atherosclerotic Arterial Fluorescence," *Circulation*, vol. 80, No. 6 (Dec. 1989).

Richards–Kortum, et al. "A Model for Extraction of Diagnostic Information from Laser Induced Fluorescence Spectra of Human Artery Wall." *Spectrochimica Acta*, vol. 45A, No. 1, pp. 87–93 (1989).

Baraga, et al. "Ultraviolet Laser Induced Fluorescence of Human Aorta." *Spectrochimica Acta*, vol. 45A, No. 1, pp. 95–99 (1989).

Andersson–Engels, et al. "Time–Resolved Laser–Induced Fluorescence Spectroscopy for Enanced Demarcation of Human Atherosclerotic Plaques." *Journal of Photochemistry and Photobiology, B: Biology*, 4 pp. 363–369 (1990).

(List continued on next page.)

*Primary Examiner*—George Manuel
(74) *Attorney, Agent, or Firm*—Sidley Austin Brown & Wood

(57) ABSTRACT

A method of analysis of organic matter, called Time-Resolved, Laser-Induced Fluorescence Spectroscopy (TR-LIFS), characterizes and discriminates certain matter, such as tissue, by investigating the fluoresence response of the protein and lipid fluorophore components in both the spectral domain and time domain. This method is more robust than prior methods as (1) can investigate the matter at muplitple wavelengths and even across an entire spectrum and (2) is more sensitive to picking up weaker fluorescence signals such as that from lipids. A detailed study of the use of TR-LIFs for the charaterization of arterial wall tisse is described. A system and instrumentation for practicing the novel method is also disclosed.

17 Claims, 23 Drawing Sheets

OTHER PUBLICATIONS

Baraga, et al. "Laser Induced Fluorescence Spectroscopy of Normal and Atherosclerotic Human Aorta Using 306–310 nm Excitation." *Lasers in Surgery and Medicine,* 10:245–261 (1990).

Andersson–Engels, et al. "The Use of Time–Resolved Fluorescence for Diagnosis of Atherosclerotic Plaque and Malignant Tumours." *Spectrochimica Acta,* vol. 46A, No. 8, pp. 1203–1210 (1990).

Andersson–Engels, et al. "Malignant Tumor and Atherosclerotic Plaque Diagnosis Using Laser–Induced Fluorescence." *IEEE Journal of Quantum Electronics,* vol. 26, No. 12 (Dec. 1990).

Andersson–Engels, et al. "Fluorescence Characteristics of Atherosclerotic Plaque and Malignant Tumors." *SPIE* vol. 1426 Optical Methods for Tumor Treatment and Early Diagnosis: Mechanisms and Techniques (1991).

Gindi, et al. "Neural Network and Conventional Classifiers for Fluorescence–Guided Laser Angioplasty." *IEEE Transactions on Biomedical Engineering,* vol 38, No. 3 (Mar. 1991).

Richards–Kortum, et al. "476 nm Excited Laser–Induced Fluorescence Spectroscopy of Human Coronary Arteries: Applications in Cardiology." *American Heart Journal,*vol. 122, No. 4, Part 1 (Oct. 1991).

McAvoy, et al. "A Comparison of Neural Networks and Partial Least Squares for Deconvoluting Fluorescence Spectra." *Biotechnology and Bioengineering,* vol. 40, pp. 53–62 (1992).

Oraevsky, et al. "XeC1 Laser–Induced Fluorescence of Atherosclerotic Arteries/Spectral Similarities Between Lipid–Rich Lesions and Peroxidized Lipoproteins." *Circulation Research,* vol. 72, No. 1 (Jan. 1993).

Maarek, et al. "Time–Resolved Laser–Induced Fluorescence of Arterial Wall Constituents: Deconvolution Algorithm and Spectro–Temporal Characteristics." *SPIE—The International Society for Optical Engineering* vol. 2980, pp. 277–285 (Feb. 1997).

Maarek, et al. "Characterization of Atherosclerotic Lesions with Laser–Induced Time Resolved Fluorescence Spectroscopy." *SPIE—The International Society for Optical Engineering,* vol. 3250, pp. 180–187 (Jan. 1998).

Marcu, et al. "Time–Resolved Laser Induced Fluorescence of Lipids Involved in Development of Atherosclerotic Lesion Lipid–Rich Core." *SPIE—The International Society for Optical Engineering,* vol. 3250, pp. 157–167 (Jan. 1998).

French, et al. "Two–Dimensional Fluorescence Lifetime Imaging for In Vitro and In Vivo Application." *SPIE—The International Society for Optical Engineering,* vol. 3250, pp. 149–157 (Jan. 1998).

* cited by examiner

NORMAL WALL

TYPE II (FATTY-STREAKS)

TYPE III (PREATHEROMA)

TYPE IV (ATHEROMA)

TYPE V (FIBROATHEROMA)

TYPE VI (COMPLICATED LESIONS)

TIME-RESOLVED, LASER-INDUCED FLUORESCENCE FOR THE CHARACTERIZATION OF ORGANIC MATERIAL

BACKGROUND OF THE INVENTION

1. Field of the Invention

This invention relates to the use of ultraviolet laser-induced spectroscopy for analysis of mammalian tissue and, in particular, to the application of time-resolved, laser-induced, fluorescent spectroscopy for the characterization of tissue based upon the lipids and protein components in the tissue.

2. Description of the Related Arts

Laser-induced fluorescence spectroscopy (LIFS), and its applications to the medical field, diagnostic chemistry and other fields, have significantly evolved during the past 20 years. The increased interest in LIFS appears to be due to its ability to reveal both qualitative and quantitative information with respect to organic matter composition. Among the spectroscopic techniques, LIFS introduces several advantages, such as wavelength tunability, narrow bandwidth excitation, directivity, and short pulses excitation. LIFS selectively and efficiently excites the fluorophores in organic matter and greatly improves the fluorescence selectivity and detectability. For these reasons, LIFS techniques have found many applications in the above described fields.

Essentially, when ultraviolet (UV) laser light at a preselected frequency radiates upon, or excites, certain organic material, the return light that is reemitted from the material contains large amounts of information about the structural features and composition of the material. Several goals for the field of LIFS have been to extract this information 1) in a way that is sensitive enough to make fine and ultrafine distinctions between samples that have been previously difficult to distinguish—i.e. improved characterization; 2) rapidly, and even in real time, to those interested in analysis of the matter; 3) in a format that is readily interpretable or pre-interpreted via computer-assisted technologies; 4) at a low cost and 5) with tools (instruments) that are appropriate for the environment in which they are used (e.g. portability, small size). Ideally such a LIFS method and system would possess all of these characteristics.

Laser-induced fluorescence emission can be conveniently divided into its static (steady-state) and dynamic (time- and frequency-domain) forms. The static form provides information of particular features such as: 1) intensity (e.g., concentration of species, quenching of species); 2) spectral distribution (e.g., information on the local environment surrounding the fluorophore, number of emitting components); and 3) polarization/anisotropy (e.g., average size of rotationally mobile species, protein-ligand binding). The dynamic form furnishes information such as: 1) excited-state intensity decay or fluorescence lifetime (e.g., it can resolve static emission into contributions from the individual fluorophores, study kinetic processes, elucidate origin of quenching processes); and 2) anisotropy (e.g., detailed reorientational dynamics of nonspherical rotors).

Steady State LIFS

The detection and the classification of organic matter have been mostly based on analysis of steady-state spectra. For example, in the bioengineering field, several studies introduced the idea of incorporating spectroscopic guidance into clinical fiber optic system to guide angioplasty systems. This technique provides an "integral" spectrum over time which gives information about emission availability and identification. The spectrum can be recorded with the help of an Optical Multichannel Analyzer (OMA) or by a scanning monochromator. Generally, scanning the spectrum by means of a monochromator is more convenient, although at a specific time only the light of a particular wavelength is recorded. This disadvantage is compensated by the superior sensitivity of photodetectors available and by their linear response in contrast to the diode array used by an OMA system. However, with steady state systems, the time dependence of emission and the potential information contained therein are ignored.

Time-Resolved LIFS (TR-LIFS)

TR-LIFS is a less explored technique for investigation of organic matter fluorescence. However, the progress of short (nanoseconds) and ultra-short (picoseconds) pulsed lasers has generated a growing interest in this field. For example, fluorescence decay of various amino acids (i.e., tyrosine, tryptophan and phenylalanine) has been an important analytical tool for protein structure and environment studies. By monitoring the fluorescence lifetime, information about the structure of the protein can be extracted. This information can be complementary to spectral information when complex biological systems, such as tissue samples, are investigated.

TR-LIFS records information regarding the emission (fluorescence pulse response) which occurs in a short time interval after the stimulating event (excitation pulse). Therefore, it permits separation of "early" (usually direct excitation of short-lived states or very rapid subsequent reactions) and "late" (usually from long-lived states, delayed excitation by persisting electron populations or by reactions which follow the original electron process) processes, referred to as the stimulus time. Fluorescence lifetime is defined as the time required for the fluorescence emission to decay to 1/e of its initial intensity. Direct measurements of fluorescence lifetime is based on the assumption that this process follows first-order kinetics quantitatively described by equation:

$$I_t = I_0 e^{-t/\tau}$$

where $I_0$ and $I_t$ are the fluorescence intensities at times zero and $\tau$, respectively.

The measured fluorescence decay of a fluorophore excited by a short pulse of light is a convolution of the excitation pulse shape (distorted by the detection system) with the true fluorescence decay (fluorescence impulse response function (FIRF)):

$$y(t) = \int_0 I_f(\tau) x(t-\tau) d\tau$$

Since accurate determination of the fluorescence impulse response is an important issue for time-resolved studies, numerous deconvolution techniques, such as Least-squares iterative reconvolution method, method of moments, Laplace Transforms, and Fourier Transforms have been developed and are well known in the art.

Application to the Characterization of Diseased Tissue

Atherosclerosis, a progressive disease of blood vessels, is reported to be the leading cause of death during middle and late adulthood in economically advanced societies. It has predilection for the critical arterial beds (coronary, cerebral and aortoiliac) and leads to critical events such as myocardial infarction, stroke, and ischemic gangrene of the extremities. Intensive efforts have been made to characterize atherosclerotic lesions in clinical situations. The main task for a technique designed to perform a clinical classification of the lesions is to picture as closely as possible the histological classification. The resulting information could then be used to accurately determine a treatment for a specific lesion type. The same holds true for other tissue diseases such as tumors. Although various techniques have been employed for clinical classification and imaging, clinical assessment of atherosclerotic lesions has been limited. Some have evaluated aneurysms and estimation of severity of stenosis. However, prevention of complicated lesions that lead to critical events, such as acute coronary syndrome, requires early detection of lesions and assessment of lesions extent. With respect to this issue, recent reports of American Heart Association have suggested that clinical danger is not very well correlated with the degree of stenosis or plaque size, but rather with plaque composition. The reports have emphasized the actual need for (1) quantitative data on size and consistency of the lipid-rich core of the fibrous plaque; and (2) greater sensitivity of imaging methods to detect and measure the components of small and thin fibrous plaques, especially those with relatively large lipid-rich centers which are likely to lead to serious clinical events such as rupture.

One research team from M.I.T. has identified that it is possible to diagnosis the presence of atherosclerosis in the human artery wall with the application of time resolved fluorescence spectroscopy. See Baraga et al. "Ultraviolet Laser Induced Fluorescence of Human Aorta, *Spectrochim.* Acta 45:95–99, 1989; and U.S. Pat. No. 5, 419,323 to Kittre II et al., and assigned to M.I.T. Others have put forth efforts to improve predictive and diagnostic methods of malignant tissue.

Unfortunately, these studies tended to focus upon the study of the known intrinsic fluorophores in tissue matter, namely collagen and elastin, but generally ignored the effect of lipids in the matter. Another primary drawback of the TR-LIFS (time domain) methods described in the literature has been one of lack of robustness and sensitivity. While the early studies of the composition of a variety of matter using TR-LIFS have shown promise, these described methods have been limited to binary classifications, that is, to crudely identify merely whether or not a particular substance of interest is present in the sample. Moreover, one reason for the limited application of fluorescence spectroscopy for tissue diagnostics is that the measured fluorescence is distorted by the effects of tissue optical properties (i.e., absorption and scattering).

Accordingly, a more precise and sensitive methodology is needed that can discriminate between a given tissue type in its varying stages of disease. For example, a TR-LIFS technique that can discern between the eight types of lesions categorized by the American Heart Association in the progressive heart disease of atherosclerosis, would be a tremendously valuable supplement to the above described binary classification systems.

Another drawback with prior TR-LIFS methodologies is that they tended to study the fluorescent tissue characteristics only at a limited number of discrete wavelengths. Much more robust information about tissue structure and condition can be gleaned with analysis of the tissue across an entire spectrum of wavelengths.

Thus a need exists for a sensitive method and system capable of quantitatively, as well as qualitatively, analyzing all of the influential fluorescent tissue components (collagen, elastin and lipids) that contribute to the character of tissue in their normal, healthy stages and in each of their classifiable diseased stages.

SUMMARY OF THE INVENTION

The present invention addresses these needs. In particular, this invention discloses a method and system for identifying the histological condition of tissue by analyzing protein and lipid components in the tissue. This is accomplished by first exciting the tissue with ultraviolet laser light of a suitable excitation wavelength and excitation intensity to cause the tissue to reemit light, and then resolving the reemitted light into component wavelengths within a predetermined bandwidth. The method then determines the time-resolved emission, or the spectro-temporal characteristics, of the reemitted light at one or more of the component wavelengths. From this emission, either one or two sets of information are then provided. It has been shown that under some circumstance intensity decay data alone, without the assistance from the spectral domain can adequately characterize some tissue, such as the arterial wall. Thus, two embodiments are disclosed. Either: (1) intensity decay data from the time resolved emission of the reemitted light at the one or more component wavelengths is provided; or (2) this same intensity decay data together with spectral intensity data representative of the intensity of the reemitted light at the one or more component wavelengths are provided. Finally, these sets of data are processed in order to analyze the histological condition of the tissue. In light of the above, characterization of tissue using time-resolved spectroscopy is greatly improved over prior systems due to its inherent greater sensitivity on the one hand, and the relative immunity of the intesity decay curve from external factors such as instrument artifacts and noise.

It should be understood that the term tissue broadly refers to any living organism that is comprised of a collection similar cells to perform a particular function. In particular, the determining the time-resolved emission includes applying an appropriate deconvolution algorithm to obtain the true fluorescence impulse response function of the reemitted light at the one or more component wavelengths. Examples of appropriate algorithms are the Laguerre expansion of kernels (introduced by Marmarelis in "Identification of Nonlinear Biological Systems Using Laguerre Expansions of Kernels," *Ann. Biomed. Eng.*, 21:573–589, 1993) or multi-exponential decay (described by Lalkowicz in "Principles of Fluorescence Spectroscopy". Plenum Press, New York, 1985).

Further, the preferred method of providing spectral intensity data is simply by integrating the intensity decay curve at each wavelength that is captured and the intensity decay data is the fast time component ($\tau 1$) and slow time component ($\tau 2$) together with the relative, normalized, amplitude component for each $\tau$ (ie. the two amplitudes, a1 and a2 combine to equal 1). In using the Lauguerre expansion of kernels for obtaining the time-resolved, pure impulse response function, the multiple exponential function is used to approximate and derive these variable. In the case of lipids and structural proteins, a double exponential function was adequate to accurately approximate the decay curve at each measured wavelength.

The processing step further comprises comparing the spectral intensity data and intensity decay data to preclassified data representative of a tissue classification system in order to characterize the tissue. The classification and comparison steps may be implemented by any of suitable processing means such as stepwise multivariate linear regression, principal component analysis, decision plane analysis, Bayes decision theory, or neural networks. Ideally, this processing step enables the automatic classification of the component without human input.

The tissue analyzed can be any type of tissue capable of being categorized by its fluorescence emissions. For example, the tissue may be a portion of an arterial wall and the processing further includes discriminating between graded levels of atherosclerotic lesions and classifying the portion of the arterial wall based upon the preclassified data representative of the tissue classification system. Alternatively, the tissue may be a tumorous mass or blood plasma. One example of a suitable classification system is the American Heart Association's progressive grading of the lesions that form in the arterial wall.

In one particular aspect of the invention, the excitation wavelength of the ultraviolet laser light is approximately 337 nanometers. This was found to be an appropriate wavelength with which to excite certain tissue so that all or most of its intrinsic fluorophores fluoresce.

In yet a more detailed aspect of the invention, the tissue can be at excited more than one excitation wavelength to collectively provide even more robust data that from a single excitation wavelength. After a subsequent application of a laser light at a new wavelength is incident on the matter, the system repeats all of the steps described above, namely resolving the light, determining the time-resolved emission of the reemitted light at one or more of the component wavelengths, obtaining spectral intensity data representative of the intensity of the reemitted light at the one or more component wavelengths, obtaining intensity decay data representative of the intensity decay of the reemitted light at the one or more component wavelengths, and processing the spectral intensity data and intensity decay data in order to analyze the histological condition of the tissue.

Further, a system, or instrument, for identifying the histological condition of tissue by analyzing protein and lipid components in the tissue is also disclosed. The system includes an ultraviolet laser excitation source that produces a light beam of a predetermined wavelength, intensity and pulse rate and an ultraviolet laser delivery and collection mechanism that transmits the excitation light beam from the source to the tissue. In one experiment, the excitation wavelength was set at approximately 337 nanometers and worked well to excite the various fluorophores in the matter being analyzed, and the laser delivery and collection mechanism was a fiber optic bundle. It also implements a light dispersing subsystem that resolves the reemitted light into component wavelengths within a predetermined wavelength range. The preferred instrument is an automatically tunable monochromator that capture and resolves the light at only one wavelength at a time. An alternative dispersing subsystem could be a spectroscope or equivalent.

A detector that detects the resolved light and converts it into an electrical signal is included and is preferably a very sensitive photo multiplier that is connected to an output slit of the monochromator. A converter, which, in the preferred embodiment is a digital oscilloscope, converts the electrical signal into a digital signal that can be manipulated by a computer system and appropriate processor to extract the spectrro-temporal data needed to analyze the subject of investigation. Thus, the processor is designed to automatically process the digitized signal to provide data indicative of the histological condition of tissue.

In an even more detailed aspect of the invention, the ultraviolet laser delivery and collection mechanism is contained in a probe which can be a catheter for in vivo application of the present invention.

Other features and advantages of the present invention should become more apparent from the following description of the preferred embodiments, taken in conjunction with the accompanying drawings, which illustrate, by way of example, the principles of the invention.

DETAILED DESCRIPTION OF THE PREFERRED EMBODIMENTS

The invention summarized above and defined by the enumerated claims may be better understood by referring to the following detailed description, which should be read in conjunction with the accompanying drawings. This detailed description of particular preferred embodiments, set out below to enable one to practice, make and use particular implementations of the invention, is not intended to limit the enumerated claims, but to serve as particular examples thereof. The particular examples set out below are the preferred specific implementations of a novel time-resolved, laser induced, spectroscopy method, system and related instruments, namely, ones that analyze and characterize lipid and protein components of organic matter. The invention, however, may also be applied to other types of systems and instruments as well.

I. The System

Figure 1:
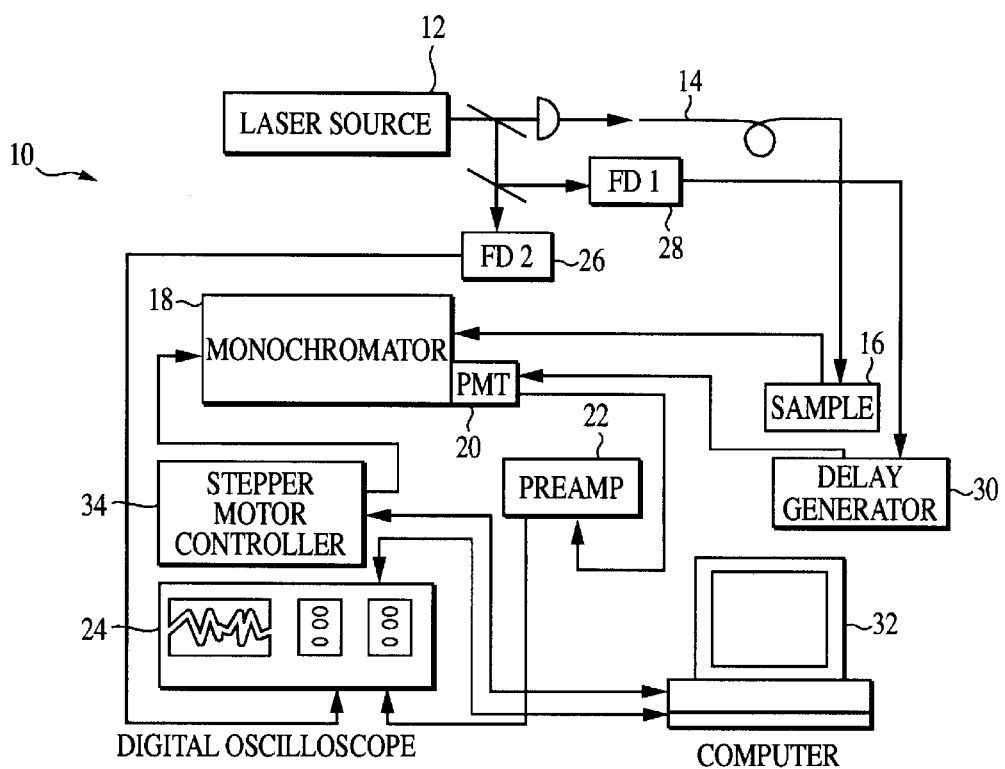
FIG. 1 is an illustrative diagram of one preferred embodiment of the basic components of the present invention.

FIG. 1 shows a basic block diagram of one preferred embodiment of the automated spectro-temporal fluorescence detection system 10 used in the present invention for the analysis of tissue and other organic substances. The output beam of the excitation source (nitrogen laser, EG&G Princeton Applied Research Model 2100: 337 nm; 3 ns, FWHM; 10 pps, repetition rate) 12 is focused into the illumination fiber of a fluorescence probe (Oriel, silica fibers) 14 and directed to the sample 16 from above. The sample fluorescence emission collected by the collection bundle in the fluorescence probe 14 was directed into the entrance slit of a scanning monochromator (Oriel, 77202; UV-VIS grating, 1200 gr/mm) 18. A gated multi-channel plate photo multiplier tube (Hamamatsu, R2024U; 0.3 ns rise-time) 20, placed at the monochomator exit slit, detects the dispersed fluorescent light beam. A long pass filter (Schott WG335) placed at the monochomator exit slit (not shown) is used to eliminate scattered laser light. The photo multiplier output 20 was amplified with a preamplifier (EG&G ORTEC, 9306;1-GHz) 22 and captured with a digital oscilloscope (Tektronix, TDS 620A; 2 Gsample/s, sampling rate) 24. A fraction of the excitation source output beam is directed with the help of two quartz beam splitters toward two fast silicon detectors 26, 2. One detector (Newport, 818-BB-20; 0.2 ns rise-time) 28 is used to trigger the gate and delay generator (EG&G ORTEC, 416A) 30, which further triggers the photo multiplier gate (5 ns, width; 5V, amplitude). The second detector (0.3 ns rise-time) 26 is used to trigger the oscilloscope 24 (to begin sweeping the photo multiplier output) and to monitor pulse-to-pulse shape and energy fluctuation of the laser.

A personal computer 32, interfaced (GPIB) with the digital oscilloscope 24 and with the monochromator stepper motor driver (Oriel, 77228) 34, is used to control: 1) data acquisition; 2) data transfer from the oscilloscope; and 3) monochromator wavelength scanning. In the preferred embodiment, a "C" language computer program was developed for this purpose. The program allows for: fast recording in one scan of both steady-state and time-resolved fluorescence spectra; selection of wavelength range and scanning wavelength steps; direct recording of fluorescent pulse integrated area; repeated recording at desired wavelengths; and scanning for identification of the wavelengths of fluorescence emission. These processing steps will be described in greater detail below.

It should be understood that the state of the art has applied a similar system for the analysis of the structural proteins, collagen and elastin in their purified forms. However, the inventors have identified that at the appropriate excitation wavelength, intensity, and pulse rate, this system is sensitive enough to study the lipid component in matter in addition to the structural proteins, which was heretofore not considered an intrinsic fluorophore capable of study using laser-induced spectroscopy for tissue analysis.

Several variations of the set up shown in FIG. 1 are possible. The sample 16 in the block diagram is not limited to one that has been extracted from its source, for example, a tissue biopsy, or a biochemical substance, that is, analyzed in a laboratory. This system can take numerous other forms for numerous other applications. For example, with the miniaturization of components (especially UV excitation sources) and the increased processing speed of computers, it is now within the realm of those skilled in the art to design a portable TR-LIFS instrument that can be introduced in an office or home setting. Further, this system can be designed into a catheter for the in vivo analysis of any human tissue, such as arterial wall, tumorous masses, or blood.

II. Data Analysis

A. Obtaining the Data in the Spectral Domain

The conventional spectral fluorescence emission (spectral domain) is computed from the measured, time-resolved fluorescence pulses by their integration as a function of time at each wavelength. In other words, the spectral intensity plot is obtained by calculating the area (or integral) under the time decay curve (the true impulse response function) at each wavelength.

Figure 2:
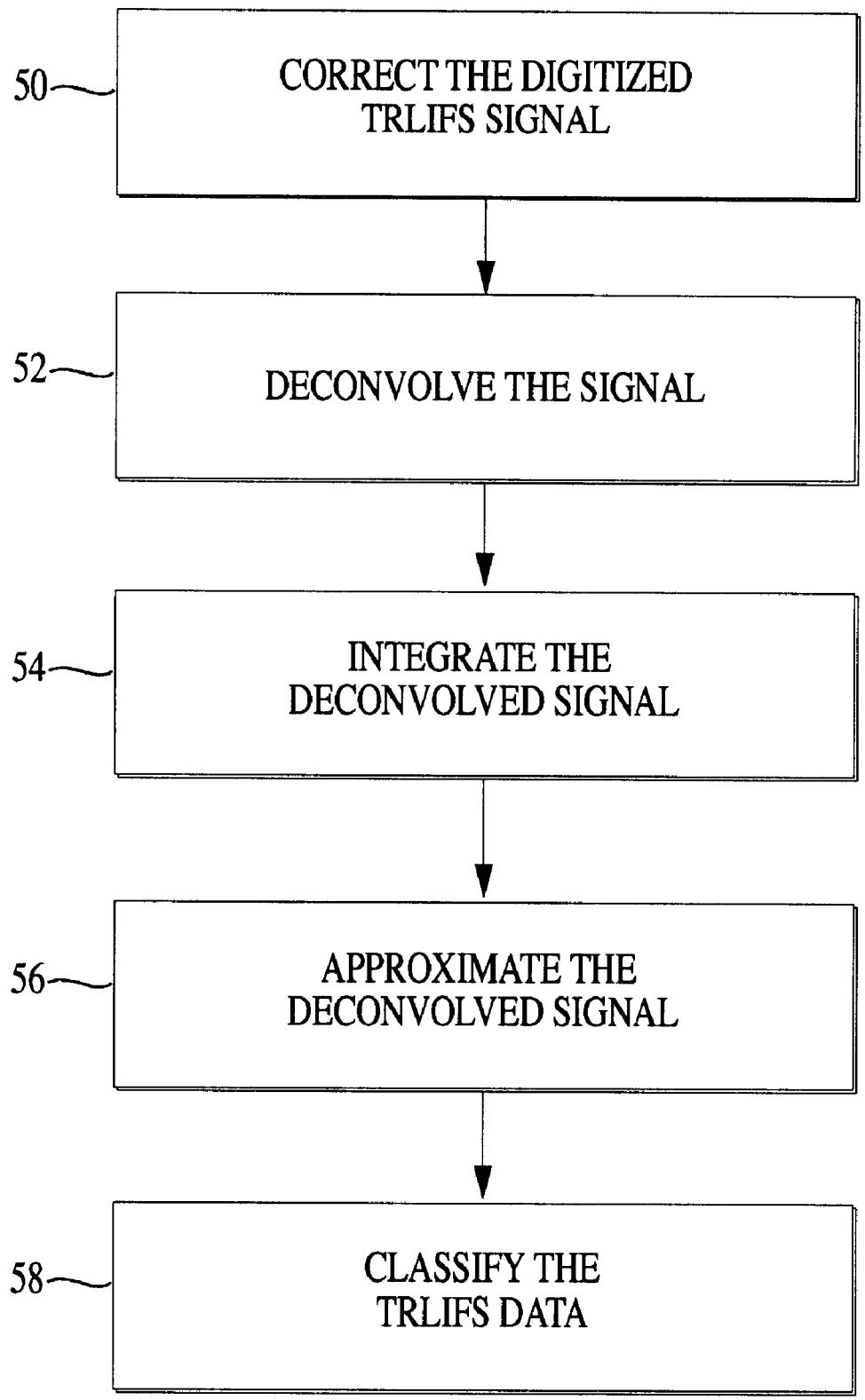
FIG. 2 is a block diagram showing the TR-LIFS signal flow and manipulation into data upon which the processor may operate.

B. Obtaining the Time Domain Data—The Fluorescence Impulse Response Function (IRF) Via Deconvolution Among the deconvolution methodologies, the inventors have opted to apply a least-squares iterative reconvolution, as it is presently believed to be the most recommended and widely used technique. As explained above, the Laguerre expansion was chosen because it is presently believed to effectively model a non-linear biological system. FIG. 2 is a flow chart that outlines one possible sequence of functions carried out by the processor that receives the raw, spectro-temporal, digitized data from the digital oscilloscope 24 and/or that is stored in the personal computer 32 that controls the hardware. In particular, in step 50 the processor corrects the signal that contains distortions due to instrumental artifacts, noise (stray light), etc. It then, in step 52 deconvolved the signal to obtain the fluorescent impulse response at each wavelength. In order to obtain useful spectral (intensity) data at each wavelength, in step 54, the processor integrates (in the mathematical sense) the impulse response function an obtain a data point that corresponds to the area under the impulse response curve. In order to make the time domain information more manipulable and manageable, in step 56 the processor approximates the signal. As discussed above, this is preferably accomplished using a multi-exponential function. Using a bi-exponential function, for example, three data points are obtained: (1) a fast decay time; (2) a slow decay time and (3) a relative amplitude contribution value for either the fast or slow component (either is acceptable because the total amplitude is normalized to the number 1. Finally, in step 58 the processor synthesizes all of the spectral and time decay data for all measured wavelengths and classifies it as certain type of matter (tissue) based upon complex, nonlinear recognition programs, such as a neural network.

III. Characterizing Pure Lipid Components Using TRLIFS

Characterizing the spectro-temporal fluorescence emissions of pure components is a first step in the characterization of organic matter comprising these pure components. The spectro-temporal fluorescence emissions of several important fluorophores have already been characterized in prior studies, see, e.g., J. M. Maarek et al., "Time-Resolved, Laser-Induced Fluorescence of Arterial Wall Constituents: Deconvolution Algorithm and Spectro-Temporal Characteristics," in *SPIE Proc.* 2980:278–285, 1997, which describes the characterization of the structural proteins collage-Type I and elastin. However, other important intrinsic fluorophores, which have been conventionally more difficult to characterize because of their low fluorescence intensity emission, namely lipids, have not been characterized in both the spectral and time domains. Since lipids are known to be important constituents of many organic substances, most importantly human tissue, it was a goal of the inventors to characterize the spectro-temporal emissions of several pure lipids known to be present in varying stages of diseased arterial walls, namely free cholesterol, cholesteryl-linoleate and cholesteryl-linoleate.

A. The Experiment

The fluorescence emissions of these lipids were measured for 360 to 510 nm wavelength range (5 nm increment, average fluorescence pulse over 16 excitation laser pulses). To determine the reproducibility of fluorescence decay, ten consecutive fluorescence transients were recorded at three wavelengths (390, 430 and 470 nm). During a single scan, the energy total fluence was mJ/mm2 (370 sec, mJ/pulse, 1.4–2.3 mm2 excitation spot area). After each measurement sequence, the monochromator was turned slightly below laser line (337 nm) and a sequence of five consecutive measurements were recorded.

As discussed above, spectral fluorescence emission intensity was recovered for each wavelength from the measured fluorescent pulse by area integration. To define the fluorescence emission of each component, we used values derived from i) two wavelength ratios $R1=I(430)/I(375)$ and $R2=I(475)/I(375)$ and ii) half width at half maximum (HWHM).

Temporal fluorescence emission, described by the fluorescence impulse response function If(tau) (IF), was determined by deconvolution of the measured fluorescence transients upon excitation laser pulse with a finite duration. The deconvolution method adopted for IF retrieving was based upon Least-Square iterative reconvolution technique combined with Laguerre expansion of kernels technique. The method was fully described above. To determine the decay characteristics, the resulting IF was approximated with a double exponential function: The contribution of each amplitude term to fluorescent transient was given by the amplitudes ratio: $Ai=ai/(a1+a2)$.

Statistical analysis was based on variance analysis tests. The tests used were: one-way ANOVA when more than two sets of data were considered; two-way ANOVA with replication when repeated measurements acquired in different conditions were compared. Additionally, a post-hoc comparison test (i.e., Tukey's) was used to supplement the results of one-way ANOVA test.

B. Results

Figure 3A:
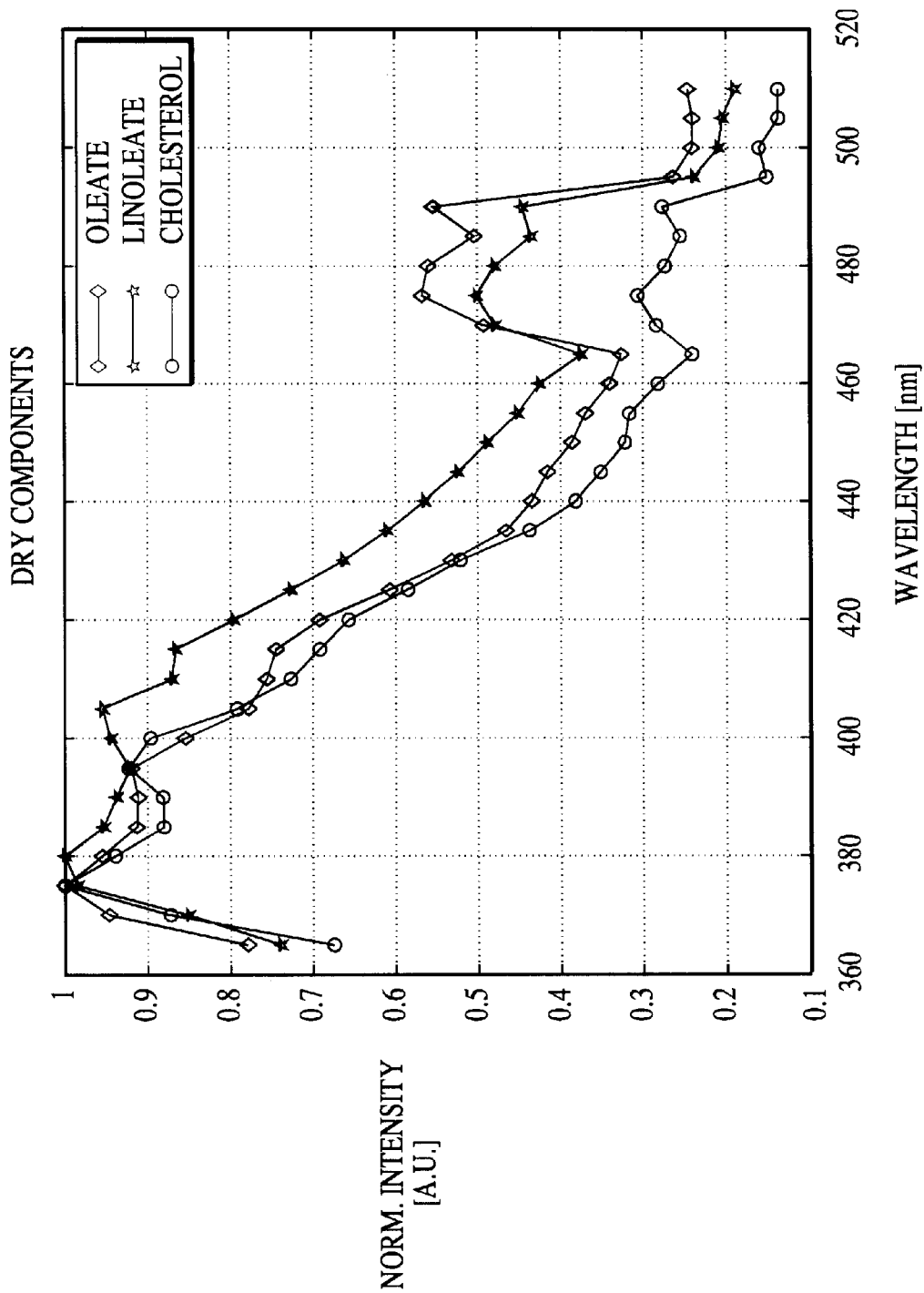
FIG. 3 illustrates two graphs of the fluorescence spectral emission for cholesteryl oleate, cholestyrel linoliate and free cholesterol for both dry and hydrated components.
Figure 3B:
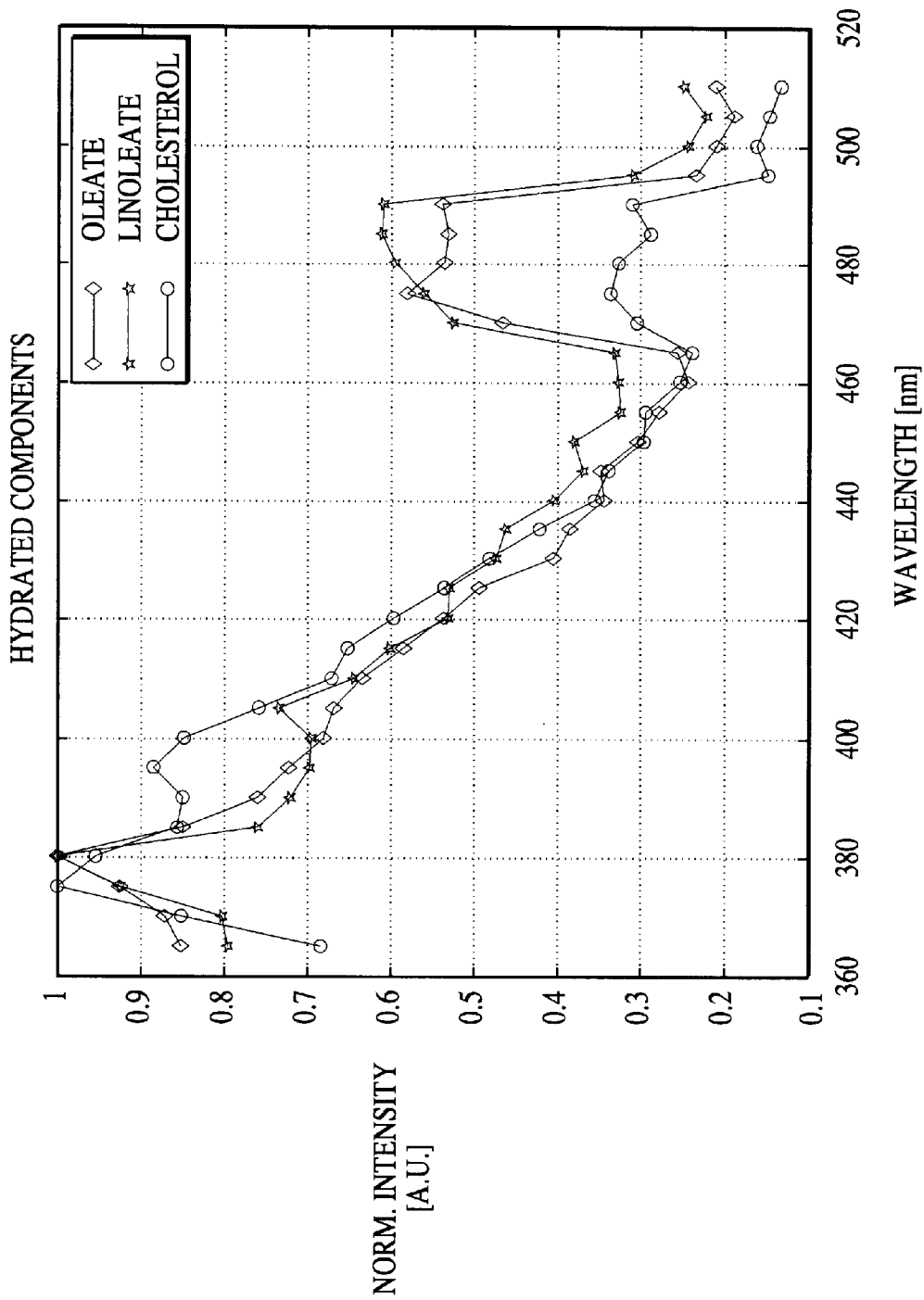

As shown in FIG. 3, in the spectral domain, the fluorescence emission of the investigated lipids was characterized by a main broad fluorescence emission in 375–410 nm wavelength range with a peal( between 375–380 nm, and a secondary emission in 470–490 nm range. These characteristics were observed for both dry (FIG. 3a) and hydrated form (FIG. 3b). However, distinctive spectral features were noticed between each lipid type and between dry and hydrated components.

Figure 4A:
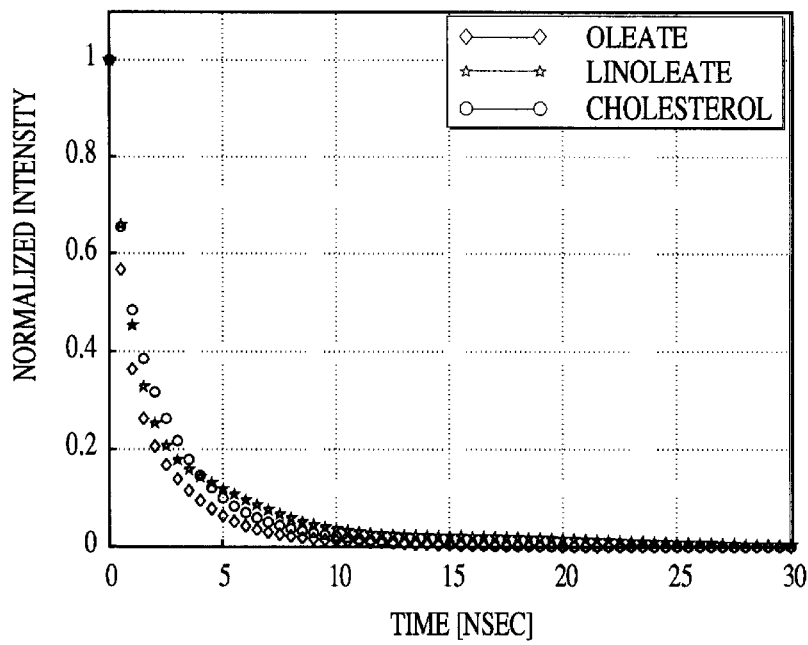
FIG. 4 illustrate four graphs displaying the impulse response function (IRF): fluorescence temporal emission of a) esterified vs. free cholesterol fluorescence decay kernel comparison (390 nm fluorescence emission; mean 10 measurements); b) Cholesteryl linoleate IRF; c) Cholesteryl oleate IRF; and d) Free cholesterol IRF.
Figure 4B:
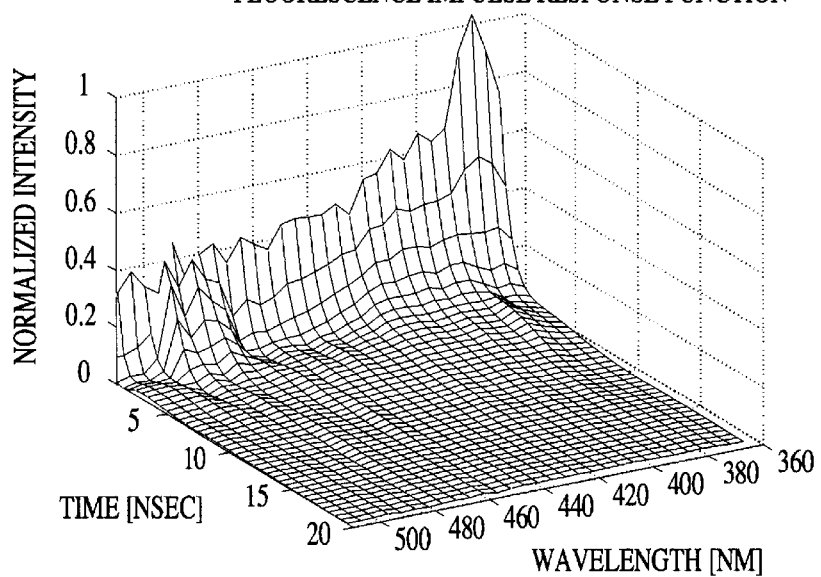
Figure 4C:
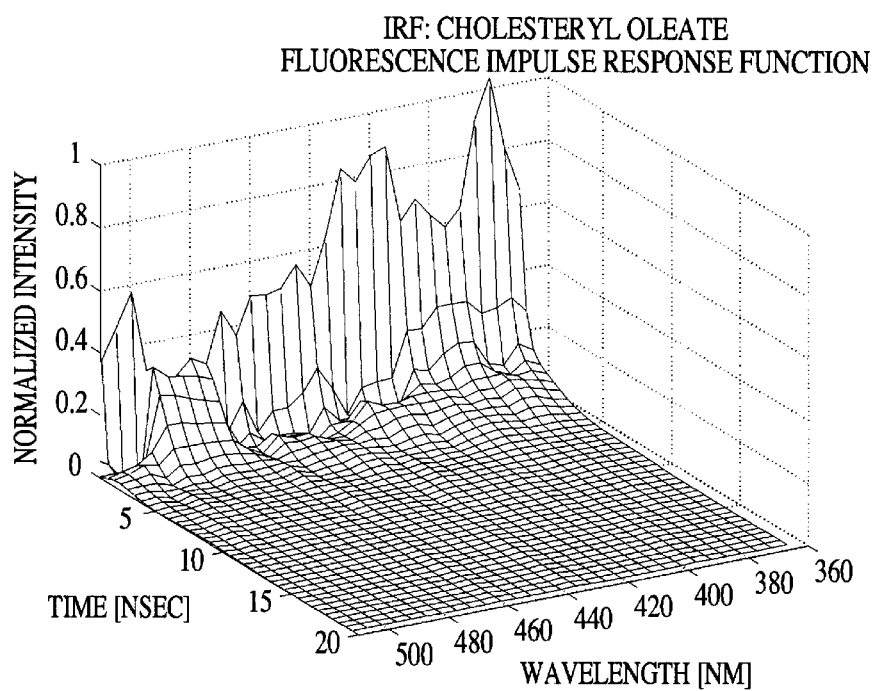
Figure 4D:
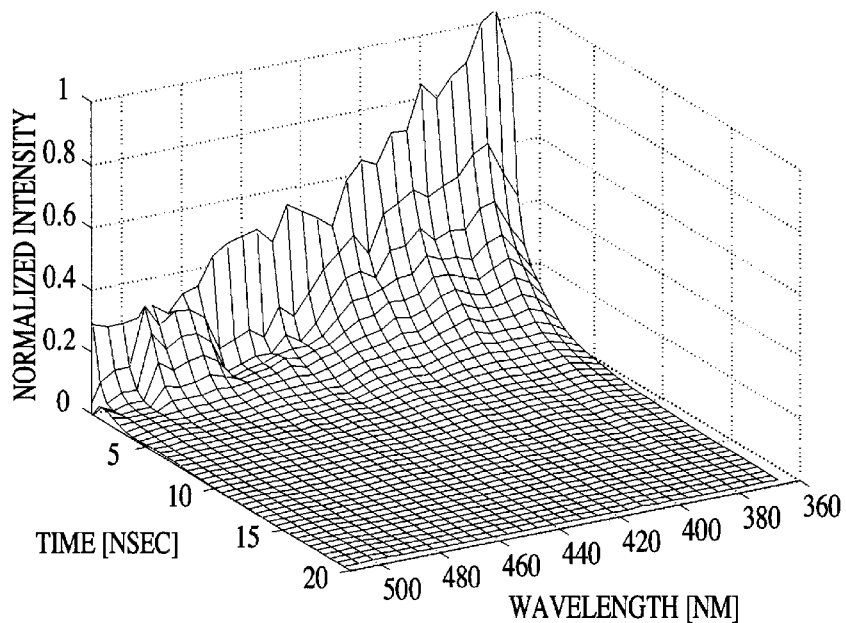

In the time domain, cholesteryl linoleate, FIG. 4a, exhibited the longest temporal decay among the three lipids: the fluorescence emission totally lasted for ~25 ns (~11 ns at 5% of initial intensity). Cholesteryl oleate was characterized by fluorescence IF lasting ~11 nsec (~6 ns) of the initial intensity whereas free cholesterol was defined by an IF lasting ~13 ns (~8 ns). The spectro-temporal fluorescence IRFs are depicted by FIGS. 4b–4d.

Figure 5A:
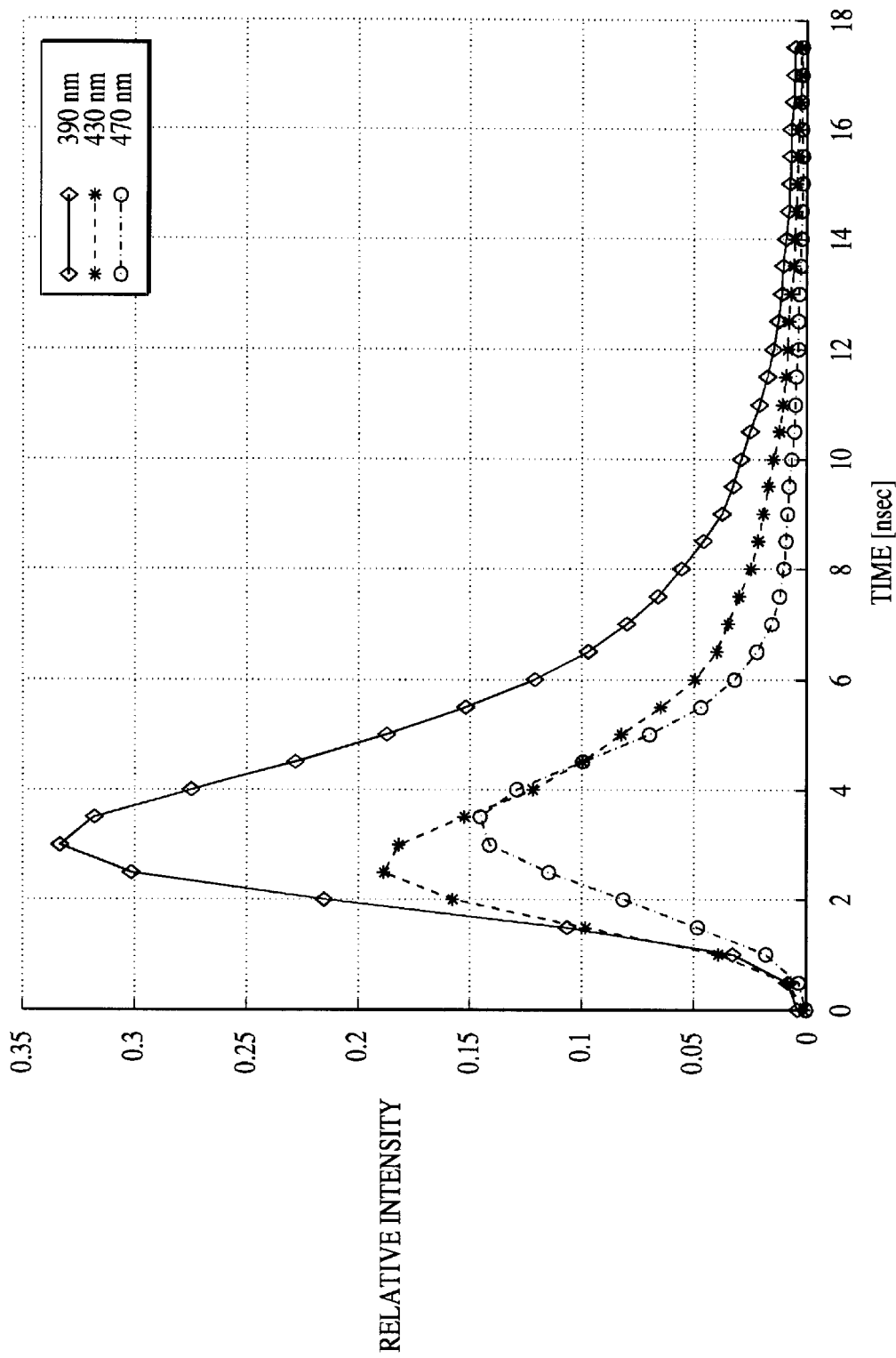
FIG. 5 displays two graphs of: a) Fluorescence pulse (e.g., cholesteryl oleate), mean 10 repeated measurements at 390, 430, and 470 nm; and b) deconvolved fluorescence IRF measurements at each of the wavelengths within the Laguerre expansion of kernel technique.
Figure 5B:
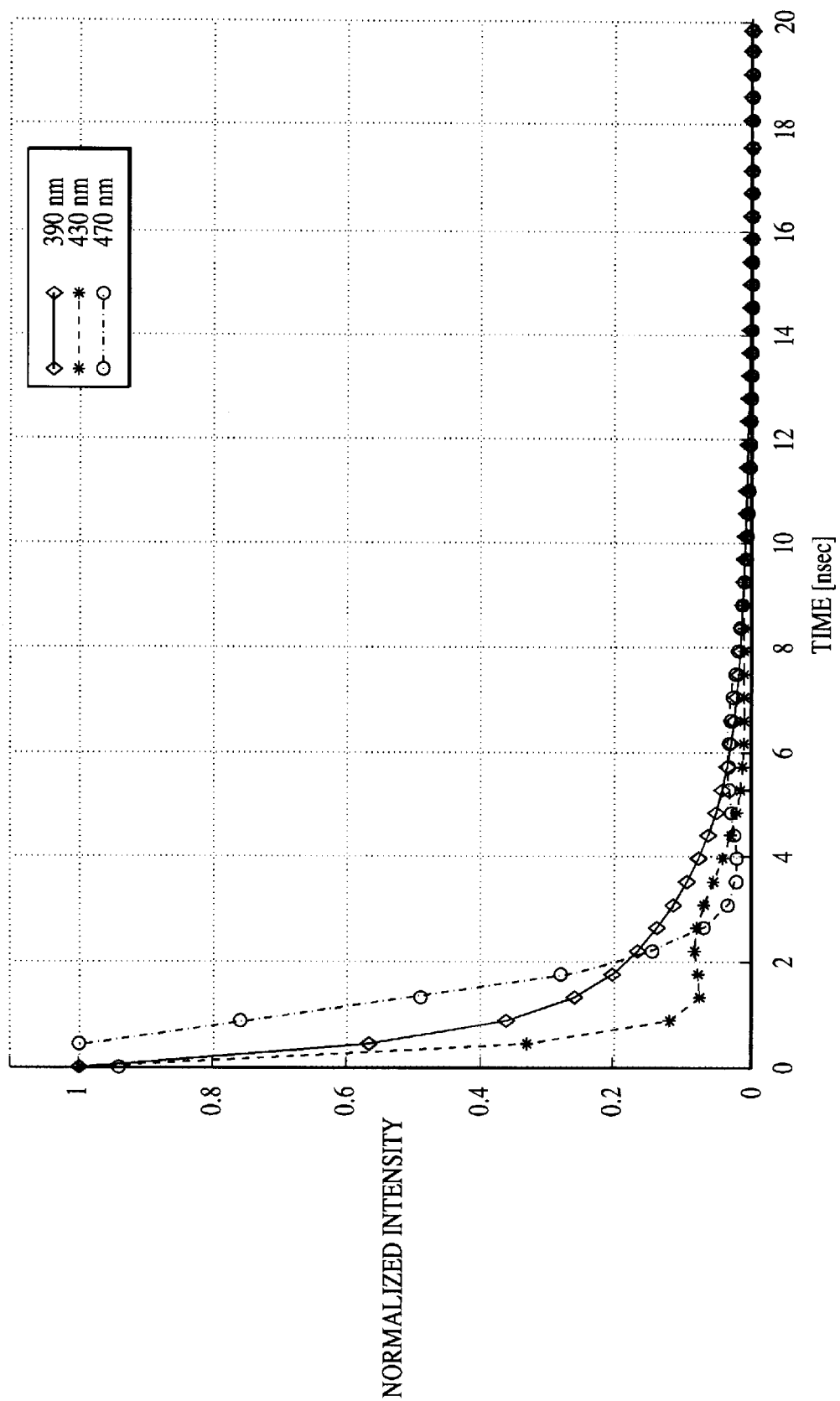
Figure 6A:
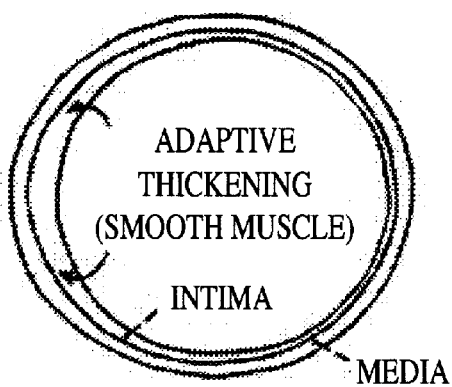
FIG. 6 illustrates schematic representations of the atherosclerotic lesion type according to the American Heart Association classification system.
Figure 6B:
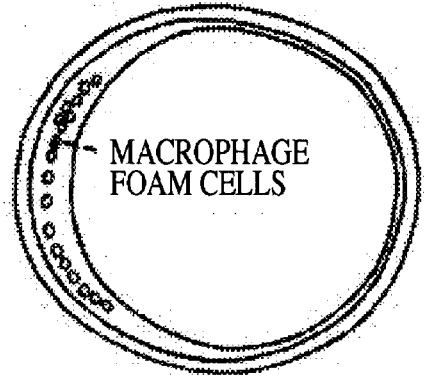
Figure 6C:
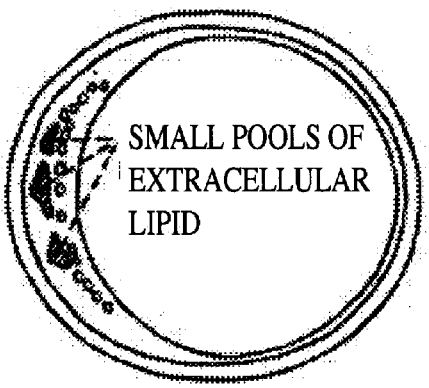
Figure 6D:
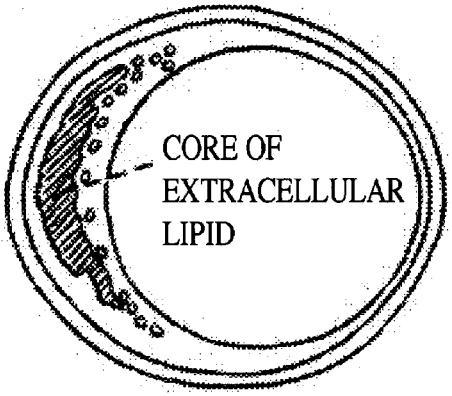
Figure 6E:
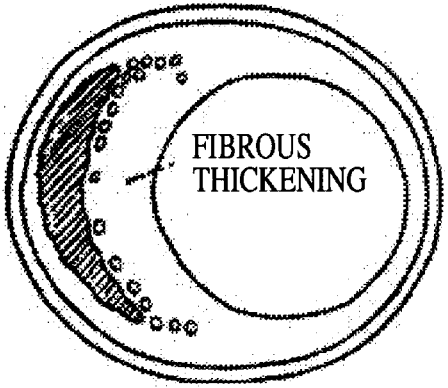
Figure 6F:
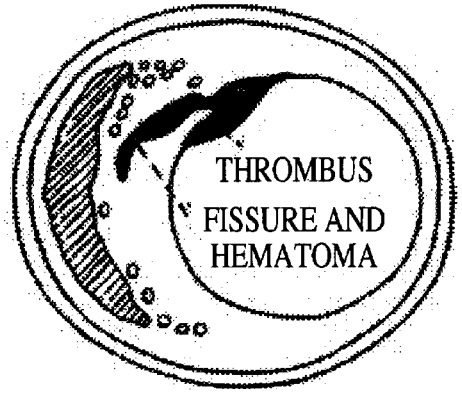

For 470–490 nm wavelength range (which corresponds to the increased spectral fluorescence emission) the pulse fluorescence reached the peak intensity later (~0.5 nsec) than at the other investigated wavelengths. See FIG. 5. This particular aspect was observed for both free and esterified cholesterol.

The fluorescence decay characteristics at 390, 430, and 470 nm (wavelengths chosen to statistically characterize the decay changes across the spectrum) are given in Tables 1–3. For dry cholesteryl linoleate (Table 1), $\tau 1$, $\tau 2$, and A1 significantly increased with wavelength (one-way ANOVA). However, no significant difference was depicted by the post comparison test (Tukey's) between $\tau 1$ and A1 at 390 and at 430 nm. For dry cholesteryl oleate (Table 2), both time constants $\tau 1$, $\tau 2$ significantly differed with wavelength (one-way ANOVA). The slow-term time constant was increased with wavelength but and its amplitude contribution significantly decreased with wavelength to less than 10%. For dry free cholesterol (Table 3), $\tau 1$ and $\tau 2$, and A1 contribution significantly increased (one-way ANOVA) with wavelengths, but no significant difference was depicted by the post comparison test (Tukey's) for $\tau 1$ at 390 and at 430 nm.

TABLE 1

Cholesteryl linoleate decay characteristics

| | dry components | | |
|---|---|---|---|
| λ[nm] | τ1 [ns] | τ2 [ns] | A1 |
| 390 | .83 ± .03 | 6.25 ± .70 | .75 ± .01 |
| 430 | .71 ± .04 | 7.55 ± .13 | .75 ± .01 |
| 470 | 1.25 ± .03 | 9.9 ± .25 | .86 ± .01 |
| P | <0.001 | <0.001 | <0.001 |

TABLE 2

Cholesteryl oleate decay characteristics

| | dry components | | |
|---|---|---|---|
| λ[nm] | τ1 [ns] | τ2 [ns] | A1 |
| 390 | .45 ± .03 | 3.45 ± .15 | .73 ± .02 |
| 430 | .30 ± .02 | 4.5 ± .10 | .90 ± .01 |
| 470 | 1.3 ± .05 | 10.50 ± .30 | .98 ± .01 |
| P | <0.001 | <0.001 | <0.00 |

TABLE 3

Free cholesterol decay characteristics

| | dry components | | |
|---|---|---|---|
| λ[nm] | τ1 [ns] | τ2 [ns] | A1 |
| 390 | .53 ± .06 | 3.0 ± .05 | .40 ± .01 |
| 430 | .54 ± .09 | 3.4 ± .01 | .56 ± .02 |
| 470 | 1.3 ± .05 | 5.8 ± .30 | .89 ± .01 |
| P | <0.001 | <0.001 | <0.001 |

For the hydrated components, similar trends were observed.

C. Observations

The spectro-temporal fluorescence emission revealed distinct features for each type of lipid (free cholesterol, cholesteryl oleate, and cholesteryl linoleate) investigated.

The spectral emission characteristics showed that: i) cholesteryl linoleate in dry form exhibited the broadest fluorescence emission, ii) all three lipids manifested an increased and delayed emission for 470–490 nm wavelength range, however the emission was significantly higher for the cholesteryl fatty-acids oleate and linoleate. These results show that the esterified cholesterol spectra can be clearly distinguished from the free cholesterol spectra in 470–490 nm range, whereas the linoleate can be differentiated from oleate and from free cholesterol at shorter wavelengths (i.e., 410–460 nm range). Additionally, free cholesterol in both dry and hydrated forms showed a secondary peak at ~395 nm. It will be appreciated that the free cholesterol spectral emission is in overall agreement to the results presented by Laifer et al "Biochemical basis for the difference between normal and atherosclerotic arterial fluorescence", *Circulation*, 80: 1893–1901, 1989. This study completes the previous work by adding the description of cholesterol esters spectra.

The temporal emission showed distinct characteristics for each type of lipid. The cholesteryl linoleate lasted longer than oleate and free cholesterol, mainly due to the slow-term decay component. Whereas the contribution of short lasting time component was significantly lower for free cholesterol relative to esterified cholesterol. Yet, changes of decay characteristics were observed across the wavelength. The most interesting aspect was the pulse fluorescence emission in 470–490 nm wavelength range for which the pulse emission was clearly shorter and delayed relative to the emission at other investigated wavelengths. This time lag suggest the existence of a species formed after excitation. Although, for 470–490 nm range, two exponential approximations were used, the very small contribution of slow lasting time component to the overall decay suggest that a monoexponential decay takes place instead. The origin of fluorescence emission for 470–490 nm range requires further investigation. However, this particular behavior could act as a fingerprint for lipid identification.

IV. The Implications

As stated above, the fluorescence emission of tissue is a composite spectrum of different types of fluorophores. For example, the emission of atherosclerotic tissue is a composite of collagen, elastin and lipids. As discussed above, these pure components have now been fully characterized in both the spectral and temporal domains using the method of the present invention. The implication of this is that, in theory, a class of organic matter that is known to comprise these fluorophores in different combinations at different stages (i.e. of disease or development) can serve as a classification system against which all matter in the same class but of unknown composition can be characterized via the method of the present invention. As discussed below, this method of classification was applied for the characterization of unknown arterial wall samples having varying degrees of disease.

V. Applications

The present invention provides an improved analysis and diagnostic tool for the characterization of organic matter that is classifiable and classified according to its lipid and protein composition. The experiments conducted that support these applications are now described in detail.

A. Tissue Analysis

The present method is designed to identify and classify the lipid and protein components of tissue in order to classify the condition of the tissue. This method was tested on a numerous arterial wall tissue samples at varying stages of disease, i.e. atherosclerosis. Preliminarily, in order to understand the biological basis of atherosclerosis and its relationship with the investigation technique used in this study, the composition of normal arterial wall vs. atherosclerotic lesions and the American Heart Association ("AHA") histological classification of arterial wall lesions are now discussed.

1. Histological Background

The normal arterial wall is divided histologically into three layers: intima, media and adventitia. Atherosclerotic lesions initially form in the intima (inner layer), while medial changes are secondary. The arterial intima is composed mainly of nonfibrous connective tissue, smooth muscle cells, elastic fibers (elastin, microfibrillar component), and collagen. Within the arterial wall, collagen and elastin are the major fibrous protein components and comprise the largest proportion of the dry weight of the tissue. Also, they are the main fluorophores in normal arteries. The proportion of each protein component varies with the type of blood vessel, the species and arterial wall layers. Generally, the values range from 20% collagen and 50% elastin in the aorta, to 40% collagen and 20% elastin in smaller arteries. However, with increasing age there is a decrease in the elastin content, relative to collagen, in the entire grossly normal aorta. Also, with age, lipids (especially cholesterol ester) start to accumulate in normal intima.

According to the new classification adopted by the AHA and used for this study, eight lesion types can be distinguish in the atherosclerosis process. As shown in FIG. 6, they are:

a) Type I lesions: very initial and most minimal changes that do not thicken the arterial wall. They are formed by small lipid deposits (intracellular and in macrophage foam cells) in the intima;

b) Type II lesions (fatty streaks): yellow-colored streaks or patches which increase the thickness of the intima by less than a millimeter. They consist of accumulation of lipid (more than in type I lesions, approx. 20–25% dry weight) mainly intracellular, in macrophage foam cells, and in smooth muscle cells. The extracellular space may contain lipid droplets, but smaller than in cell, and small vesicular particles. Chemically, the lipid consists of cholesterol esters (cholesteryl oleate and cholesteryl linoleate), cholesterol, and phospholipids;

c) Type III lesions (preatheroma): thicken the intima only slightly more than type II and do not obstruct arterial blood flow. The extracellular lipid and vesicular particles are identical to those found in type II lesions, but in increased amount (approx. 25–35% dry weight) and start to accumulates in small pools;

d) Type IV lesions (atheroma): crescent-shaped which increases the thickness of the artery. The lesion may not narrow the arterial lumen much except for persons with very high plasma cholesterol levels (for many people, the lesion can not be visible by angiography). They consist of an extensive accumulation (approx. 60% dry weight) of extracellular lipid in intima (lipid core). The lipid core may contain small clamps of minerals. These lesions are susceptible to rupture and to formation of mural thrombi;

e) Type V lesions (fibroatheroma): one or multiple layers of fibrous tissue (mainly type I collagen) are added to a Type IV lesion. They generate additional increase of wall thickness and progressive reduction of the lumen. These lesions have features that permit further subdivision: Va, the new tissue is part of a lesion with a lipid core; Vb, the lipid core and other parts of the lesion are calcified (lead to Type VII lesions); Vc, the lipid core is absent and lipid in general is minimal (lead to Type VIII lesions). Generally, the lesions that undergo disruption are Va type. They are relatively soft and have a high concentration of cholesterol esters rather than free cholesterol monohydrate crystals. Same as Type IV lesions, they can rupture and form mural thrombi;

f) Type VI lesions (complicated lesions): disruptions of the lesion surface such as fissures, erosions or ulcerations (Type VIa), hematoma or hemorrhage (Type VIb), and thrombotic deposits (Type VIc) are superimposed on Type IV and V lesions. They lead to increase lesion thickness and lumen often completely blocked. These lesions can convert to type V lesions, but larger and more obstructive;

g) Type VII lesions (calcified lesions): large mineralization of advanced lesions. Mineralization takes the form of calcium phosphate and apatite, replacing the accumulated remnants of dead cells and extracellular lipid;

h) Type VIII lesions (fibrotic lesions): mainly layers of collagen, but lack of lipid. They could be a consequence of lipid regression of a thrombus or a lipidic lesion with the extension converted to collagen. These lesions may obstruct the lumen of medium-sized arteries.

A few important known features of arterial wall lesion, related to this work are:

a) The early lesions (Type I and Type II) and the intermediate lesions (Type III) are characterized by a few and minimal changes in elastin and collagen content. Accumulation of lipid (mainly cholesterol ester) is a common feature;

b) The advanced lesions (Types IV, V, VI, VII and VIII) alter the elastin and collagen content. For instance, collagen becomes the major extracellular component of Type V and VIII lesions (30%–60% dry weight of the total protein content of some lipid-poor advanced lesions or part of advanced lesions). Depending on the location and lesion type, elastin fibers may be increased, decreased, or relocated. Degradation of elastin is a common feature which appears to be associated with lipid and calcium deposits. Also, an increase of esterified cholesterol is characteristic for Type IV and Va lesion; and c) Morbidity and mortality from atherosclerosis is mainly due to Type IV and Type Va lesions in which disruption of the lesion surface, hematoma or hemorrhage, and thrombotic deposits had developed (Type VI lesions). Such lesions may or may not be visible by cardiovascular imaging techniques, and may or may not produce clinical manifestations. These lesions may be clinically significant even when the arterial lumen is not narrowed, because the complications can develop suddenly. Therefore, prevention, detection, extension assessment and composition of complicated lesions (Type VI) are presently important clinical goals.

The purpose of this classification system, is to picture the histology as close as possible and then to precisely determine the treatment for specific lesions. Since this classification system provides an estimation of the contribution of the three primary fluorophores (elastin, collagen and lipid-rich deposits) in the arterial wall at each clinical stage, atherosclerosis was a prime medical condition with which to apply the method of the present invention was applied in order to fully characterize atherosclerotic lesions at its varying stages of progression.

Several ways of using spectral information for automatic lesion classification have been reported: evaluation of intensities ratios and spectral width at half maximum (HWHM) features, whole spectral intensity, multivariate linear regression, stepwise multivariate linear regression, principal component analysis, decision plane analysis, Bayes decision theory, and neural network, name some of these processing methods. A binary classification was mainly employed by most previous studies. More recently, Morguet et al., reported the discrimination (based on linear discriminant analysis) between five type of fluorescence spectra (media, lipid lesions, fibrous lesions, and calcified lesions in blood and saline) recorded with ongoing tissue ablation. Nevertheless, none of the previous studies investigated the use of fluorescence decay emission in the whole range of tissue spectral emission for classification of atherosclerotic lesions. The inventors succeeded to show that the TR-LIFS methodology of the present invention is an excellent tool for the discrimination of atherosclerotic lesions in the arterial wall across a range of the emission spectra.

The instrumentation used for the characterization of pure lipid components was used for this study. The aortic samples (total: 112 from 43 aortic segments (thoracic, abdominal, and ascending) from 14 subjects; subject age: 11–85 years, median 49 years) with different levels of atherosclerosis were obtained at autopsy (24–48 hrs. postmortem), cleaned and rinsed with buffered saline solution. Aortic segments were longitudinally open, snap frozen in isopentane and liquid nitrogen, and stored at −75° C. until use. Frozen segments were passively warmed at room temperature, and kept moist with saline prior to study. Thereafter, the segments were flattened and fixed with intimal surface outward on a nonfluorescent plastic board. After study, areas from which fluorescence was collected were marked with small incisions. Each sample was fixed in formalin and processed for histological examination and classification. Hematoxilin-Eosin stained 4 mm transverse paraffin sections from the marked region of each sample were examined by a pathologist and histologically classified according to the American Heart Association (AHA) classification described above. All histological section with mixed lesion type feature (e.g., Type I to Type II, Type II to Type III, etc.) were marked as having a border classification. The intimal thickness of the samples (stained section) were measured under microscope.

The spectro-temporal fluorescence response of aortic samples was measured between 360 and 510 nm (5 nm increment, average fluorescence pulse over 16 excitation laser pulses). To determine the reproducibility of fluorescence IF, ten successive fluorescence transients were recorded at three wavelengths (390, 430, and 470 nm). Each arterial sample was placed with intima towards the fluorescence probe. Before spectroscopic examination, the samples were visually examined and distinctive spot areas of normal aortic wall and/or atherosclerotic lesions were isolated for study. During a single scan, the energy total fluence delivered to each spot area was mJ/mm2 (370 sec, mJ/pulse, 1.4–2.3 mm2 excitation spot area, ~2 mm distance between investigated spot and fluorescence probe). As previously discussed, this energy total fluence was found to minimize fluorescence photobleaching of the arteries intrinsic fluorophores. The scattered laser pulse (16 pulses average) from the investigated area was measured slightly below laser line (337 nm).

2. Data Analysis a. Spectral emission: The conventional spectral fluorescence emission was determined from the measured time-resolved fluorescence pulses by their integration as a function of time at each wavelength. For each investigated arterial area, the resulted steady-state spectrum was normalized by dividing the florescence intensity at each emission wavelength by the maximum fluorescence intensity recorded in 360–420 nm wavelength range from that arterial area. This new spectrum was characterized by discrete fluorescence intensities (Iw1) that showed the variation of fluorescence intensity as a function of wavelength for each arterial area spectroscopically investigated.

b. Temporal emission: Fluorescence impulse response function (FIRF), was determined by deconvolution from the measured fluorescence transients. The deconvolution method adopted for IF retrieving was based upon Least-Square iterative reconvolution technique combined with Laguerre expansion of kernels technique as fully described above. To determine the decay characteristics, the resulting FIRF was approximated with a double exponential function. The results from univariate tests were used to identify essential differences among variables that characterize each lesion type and normal aortic wall.

Multivariate statistical analysis: Based on histopathological examination each data set from an aortic sample strictly classified was assigned to one of the five groups: Group 1 (Normal+Type I); Group 2 (Type II); Group 3 (Type III+ Type IV), Group 4 (Type V), and Group 5 (Type VI). A stepwise discriminant analysis (SPSS statistical software) was used for the following purposes:

1) to determine which combination of predictor variables (i.e., spectro-temporal fluorescence emission parameters: time and amplitude constants, and fluorescence intensity at discrete wavelengths across emission spectrum) accounts for most of the differences in the average profiles of the groups, thus one could generate a set of discriminant functions that provides the best discrimination between aortic specimens from different groups;

2) to test the validity of discriminant functions that were derived for aortic samples classification and to determine the classification accuracy for training set and cross-validated set. Also, the canonical discriminant function (generated from training set) were used to predict the group membership for the specimens with border classification. Note that, since a relatively small number of samples were available for study, a cross-validation (hold-out sample) approach was adopted instead of split-sample approach (randomly divide the samples into two groups).

Three sets of possible predictor variables ($\tau 1$, $\tau 2$, A1, and Iw1) determined for 360–510 nm wavelength range at 10 nm intervals, were tested on the aortic specimens fluorescence emission parameters:

i) Set 1: included both spectral and temporal emission characteristics information (i.e., all decay constants and fluorescence intensities; total: 64 variables);

ii) Set 2: included only temporal information (i.e., all decay constants; total: 48 variables);

iii) Set 3: included only spectral information (i.e., all fluorescence intensities; total: 16 variables).

The classification accuracy was evaluated based upon a model proposed by Sox et al., in "Making Medical Decision," Butterworths, Boston, Mass., and is incorporated herein by reference.

3. The Results

Out of 112 histological samples that underwent spectroscopic examination, 87 sections were strictly classified as: Normal, 12 samples; Type I, 21 samples; Type II, 21 samples; Type III, 8 samples; Type IV, 5 samples; Type V, 15 samples; Type VI, 5 samples. The remaining samples had border classifications: Type I–II, 16; Type II–III, 8; Type IV–V, 4. The emission spectra and all spectro-temporal parameters presented in this section represent the mean for each specimen type (normal aorta and Types I, II, III, IV, V, VI) strictly classified.

The intimal thickness of aortic specimens showed a gradual increase as a function of lesion type (Type I to Type V). For normal (median: 80 mm) and Type I (120 mm) lesions the thickness range totally overlapped, although the median value for normal aorta is smaller. For Type II lesions, intima was thicker (225 mm) but it showed a partial overlap with the thickness of normal and Type I lesions (also note the strong skewness towards lower values). For Type III (500 mm) and IV (900 mm), a significant increase of intima was found. For Type V lesions (1400 mm), the thickness of collagenous cap ranged between 500–700 mm. Compared to Type V, the thickness recorded for Type VI were found relatively smaller (1000 mm).

a. Spectro-temporal Fluorescence Emission Characterization of Aortic Lesions

Figure 7A:
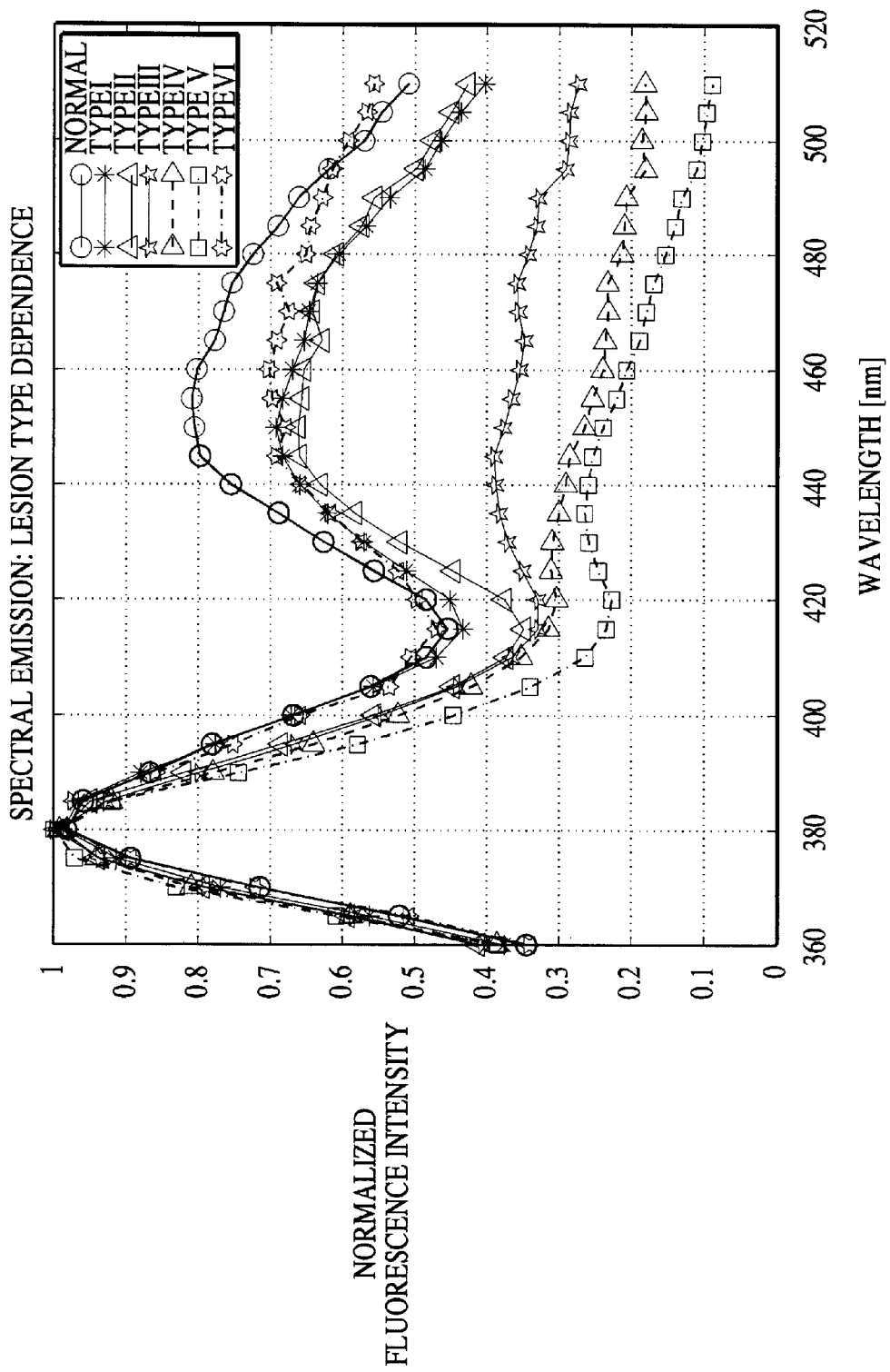
FIG. 7a is a graph showing the normalized fluorescence intensity of an aortic tissue as a function of wavelength for each.

Spectral emission of aortic specimens are shown in FIG. 7a. A main peak emission at ~380 nm was observed for normal aortic wall and for all lesion types.

Figure 7B:
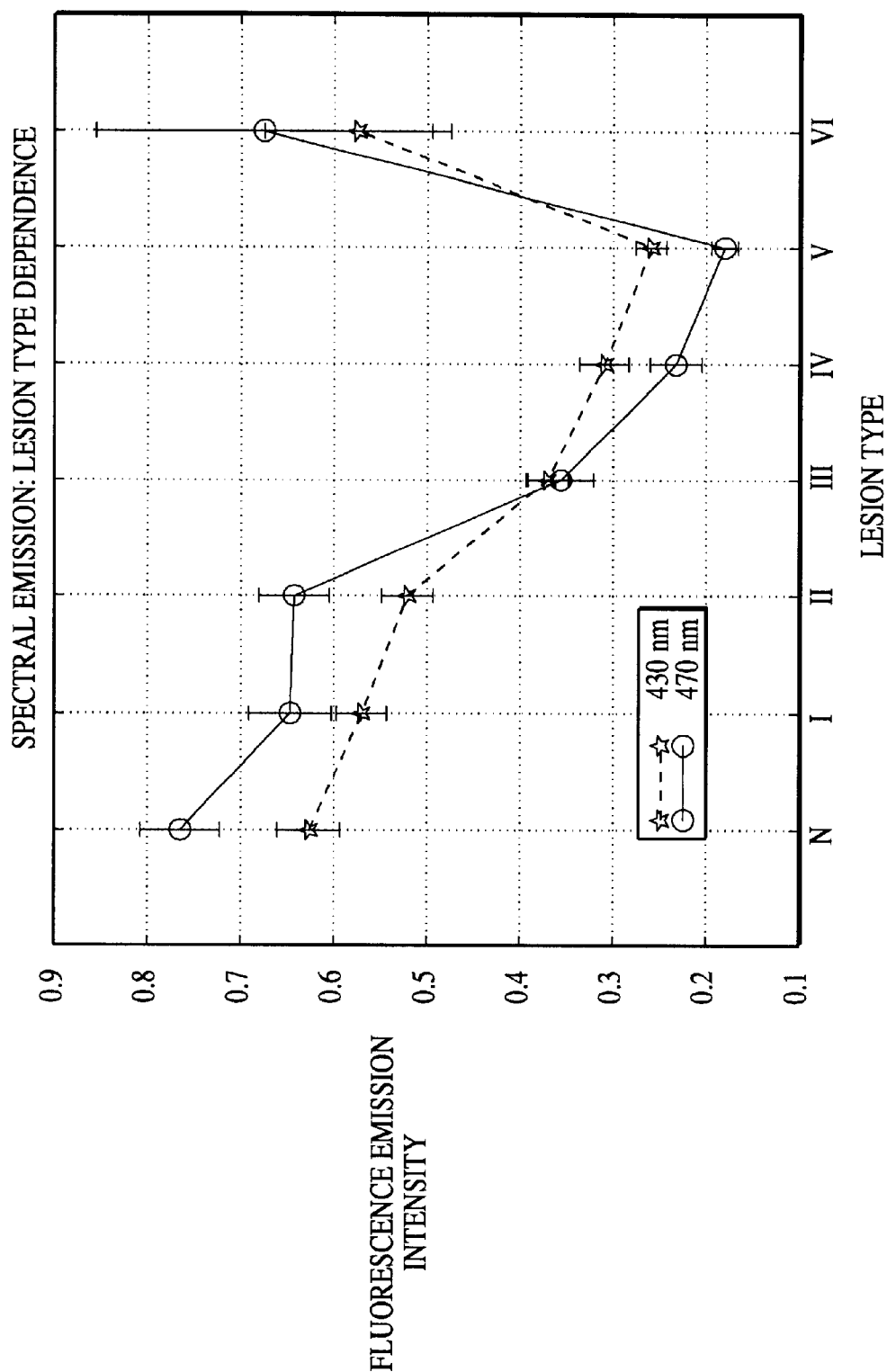
FIG. 7b is a graph showing the variation of fluorescence emission intensity ( ) at 430 and 470 nm as a function of aortic lesion type.

Normal aortic wall, Type I, Type II, Type III, and Type VI showed a broad emission over the wavelength range investigated and a secondary peak fluorescence at 440–470 nm. The height of the secondary peak was higher for normal arterial wall (~80% of the height of the main peak) relative to the height recorded for Types I, II, and IV lesions (65–70%). Types III, IV, and V lesions did not show distinct secondary peak fluorescence. Relative to their peak emission, the emission at 440–470 nm was diminished to ~40% for Type III and ~25% for Types IV and V lesions. Additionally, we observed for Type II and III lesions a slightly increased fluorescence intensity in 470–490 nm range. For spectral domain, these results suggest that the fluorescence emission at longer wavelengths is more affected by the type of the lesion. Note also the valley that modulate the emission spectra of all lesions at ~415 nm (more obvious for normal, Type I, II, VI). The variation of fluorescence emission at 430 and 470 nm as a function of lesion type is given in FIG. 7b. A significant change (P<0.001) of emission intensity at 430 and 470 nm (I430, I470) was observed among lesions. Fluorescence emission considerably decreased as a function of lesion type from normal aorta (e.g., I470:%) to Type V (%) lesion. The emission intensity of Type VI lesion was in the range of normal tissue and initial lesions and showed a large variability (%).

The time-resolved fluorescence IF's of aortic specimens are represented by FIG. 8. Fluorescence emission of normal aortic wall (FIG. 8a) lasted for ~20 ns and approached 5% of its initial intensity in about ~11 ns at the wavelengths region of the main peak emission (e.g., 390 nm). Similar trends were observed across all the wavelengths. Fluorescence emission of Type I lesions (not shown here) evidenced very similar characteristics to the emission of normal tissue. As seen in FIG. 8b, the emission of Type II lesions decayed in ~21 ns (10.5 ns at 5% of peak intensity).

Figure 8A:
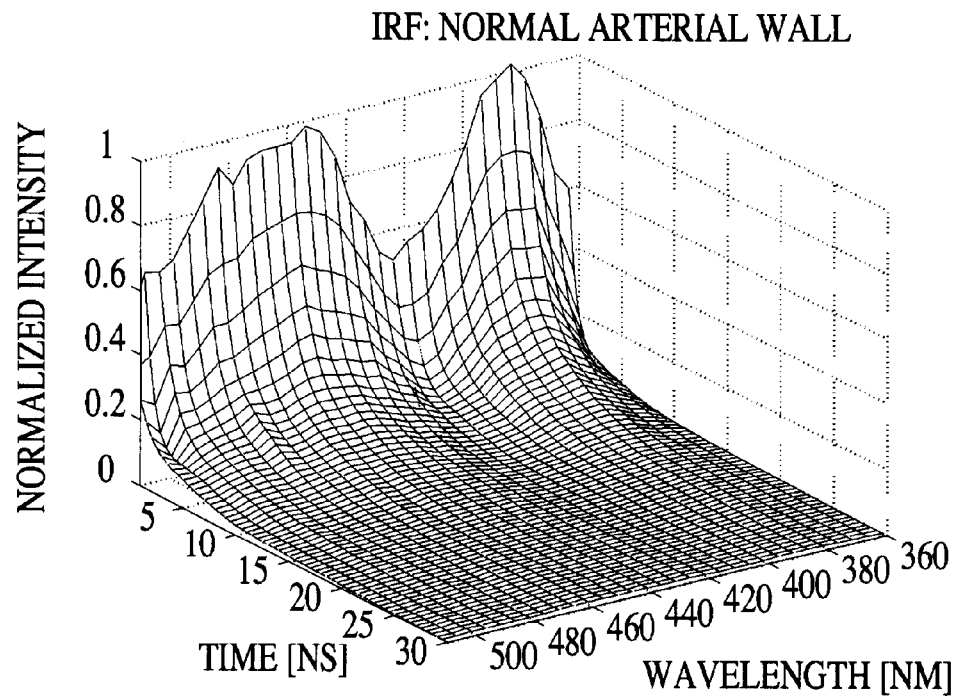
FIG. 8 are typical fluorescent impulse response function graphs for a) Normal arterial wall; b) Type II lesions; c) Type III lesions; d) Type IV lesions; e) Type V lesions; f) Type VI lesions.
Figure 8B:
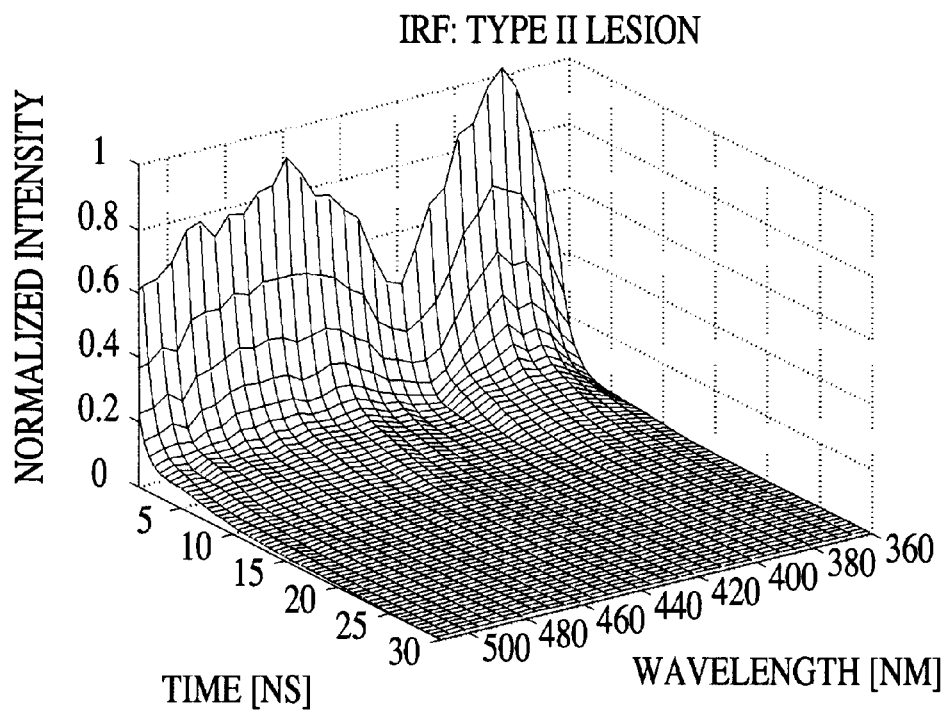
Figure 8C:
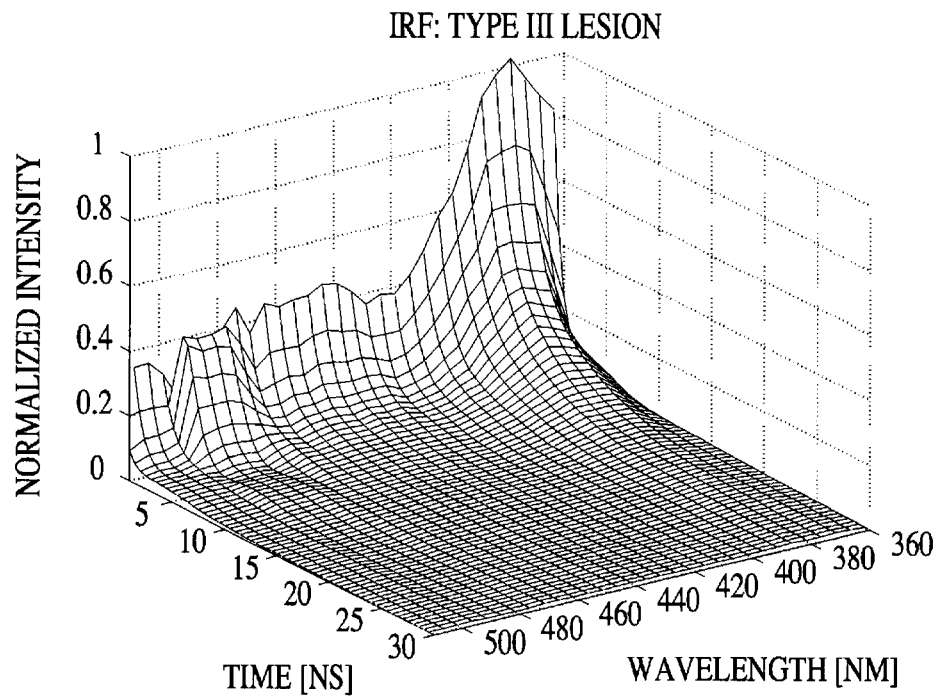
Figure 8D:
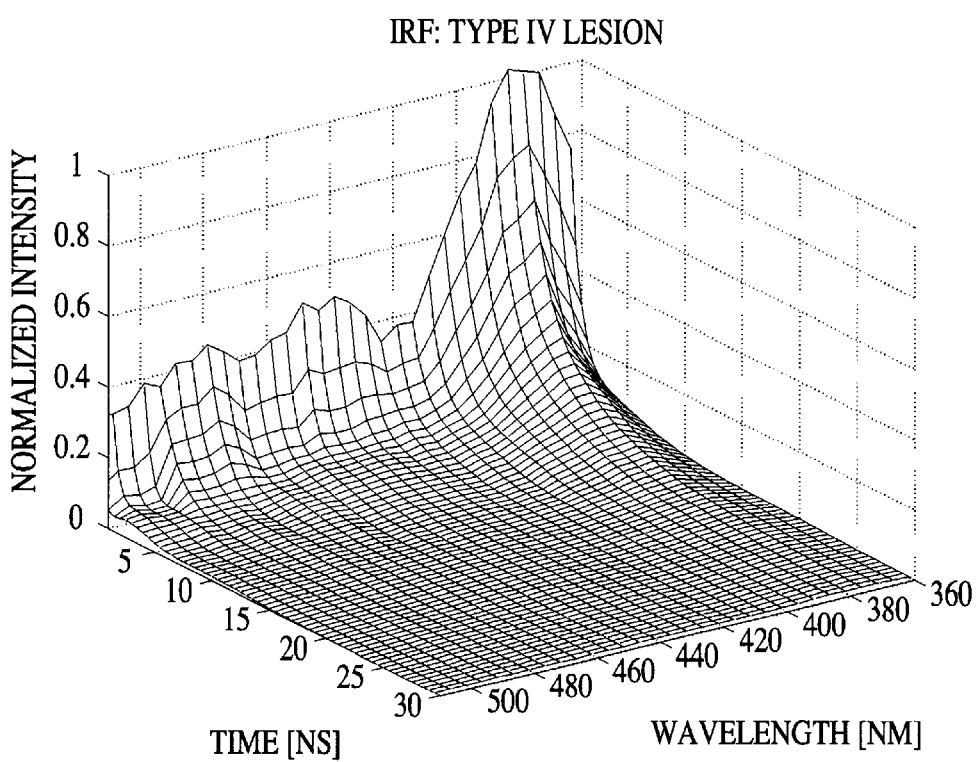
Figure 8E:
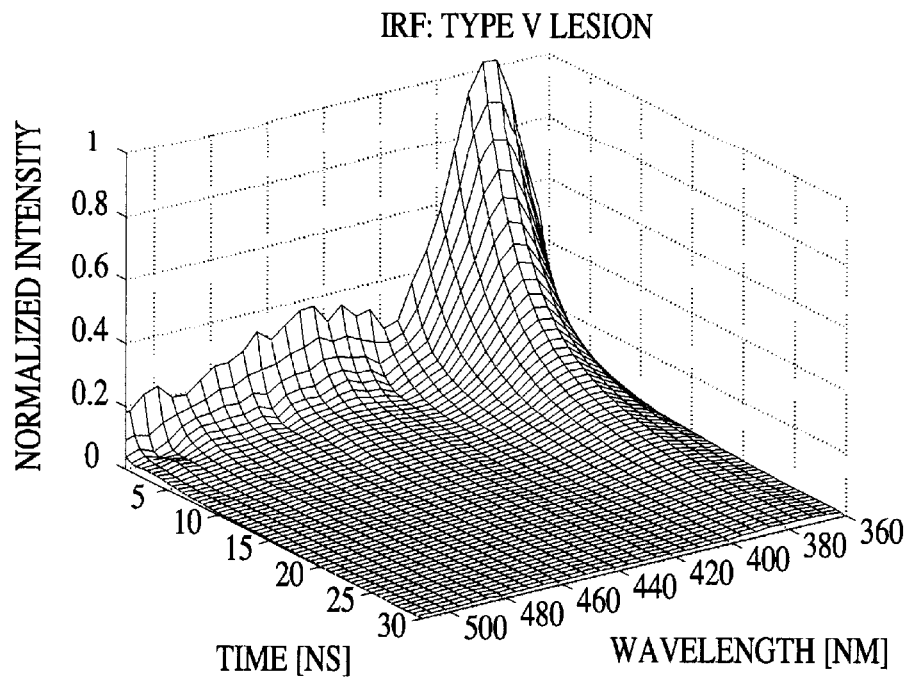
Figure 8F:
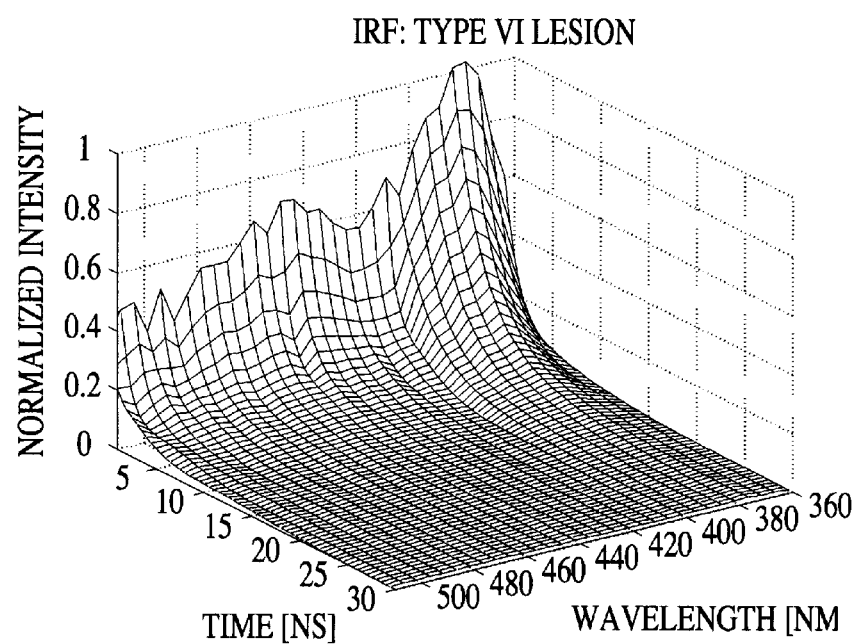

Type III, FIG. 8c, and type IV, FIG. 8d emission decay exhibited similar characteristics. Relative to Type II, the Type III+IV emission lasted longer (III: ~23.5 ns; IV: ~25 ns) with a decay to 5% peak intensity at ~13 ns and ~14 ns respectively. Also, shorter emission was observed at longer wavelengths (e.g., 430 nm decay to 5%: III, ~11 ns; IV, ~12 ns; 470 nm decay to 5%: III, ~10 ns; IV, ~11 ns). For Type III and a few Type IV lesions fluorescence emission at 470–490 nm wavelength range was slightly delayed in time with 0.5 ns. The temporal emission of Type V lesions (FIG. 8e) lasted for ~29 ns and reached 5% of initial intensity in ~16 ns at the wavelengths of the main peak and in ~13 ns at longer wavelengths. Type VI lesions decay (FIG. 8f) was shorter relative to Type V. The emission lasted for ~25 ns and it reached 5% of peak intensity in ~13 ns at peak emission spectral region at in ~12 ns at longer wavelengths.

Figure 9A:
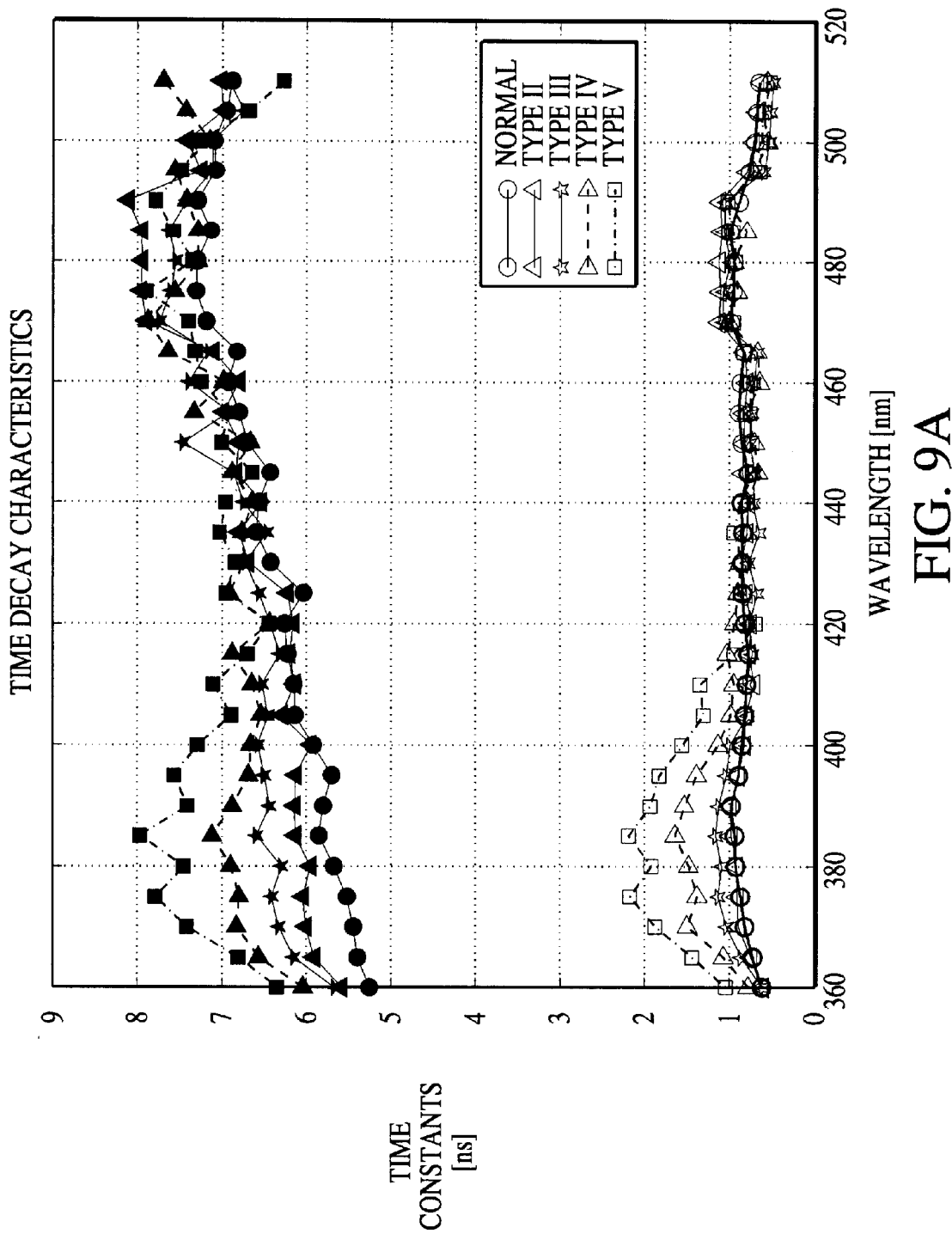
FIG. 9 shows the time decay and amplitude contribution of A1 for normal aortic wall, Type II, Type III, Type IV, and Type V aortic lesions, and how they change as a function of wavelength.
Figure 9B:
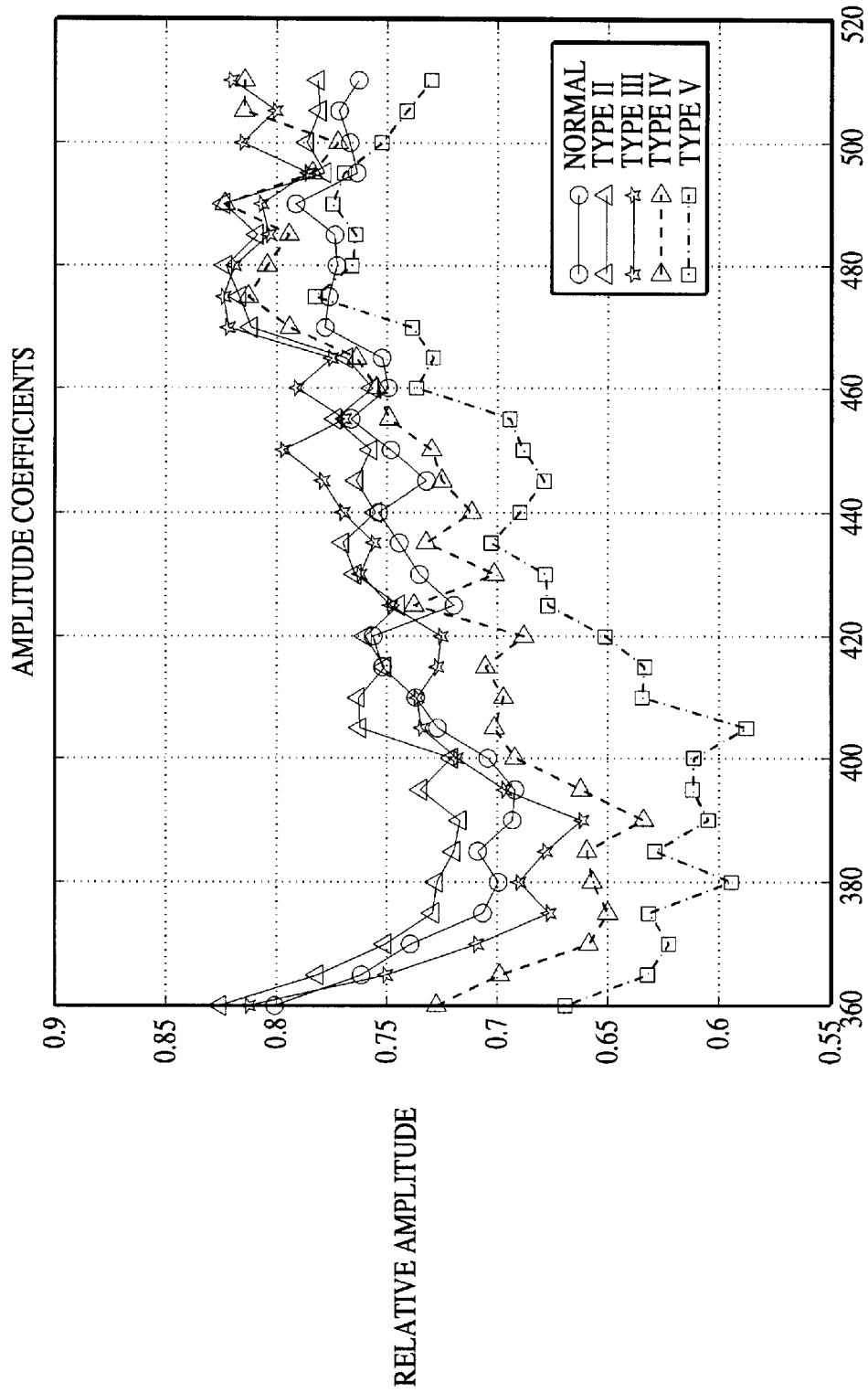

The decay characteristics (fast- and slow-terms time constant; fast-term amplitude contribution) FIG. 9 are summarized as follows:

i) Normal aorta showed a relatively constant fast-term time constant $\tau 1$ FIG. 9a, over the wavelength range that we investigated (ns), whereas its amplitude contribution A1, FIG. 9b, slightly increased with wavelength (from at 380 nm to at 480 nm). The slow-term time constant τ2 gradually increased with wavelength from ns at 380 nm to ns at 480 nm.

ii) Type II lesions exhibited similar trends to those of normal aorta except for the following differences: an increase of both τ1 (ns) and τ2 (ns) in 470–490 nm range, an overall increase of A1 contribution across the spectrum, especially in 470–490 nm range (at 480 nm), and a slightly increase of τ2 at shorter wavelengths (ns at 380 nm);

iii) Type III, IV, and V showed a gradual increase of τ1, τ2 (e.g., at 380 nm, Type III to V: τ1, ; τ2, , , ) and decrease of A1 (,, ) below 420 nm. Above 420 nm the values of both time constants τ1 and τ2 were not noticeable different from the values observed for the early lesions. However, the values of short lasting term contribution A1 for Type IV and V were decreased above 420 nm.

Overall, for time domain, these trends suggest that the decay characteristics of fluorescence emission at shorter wavelengths are more affected by the type of the lesion. Note also that, the emission at 360 and 365 nm probably contained a fraction of the laser pulse (suggested by the increased contribution of the fast-term time component at these wavelengths).

Figure 10A:
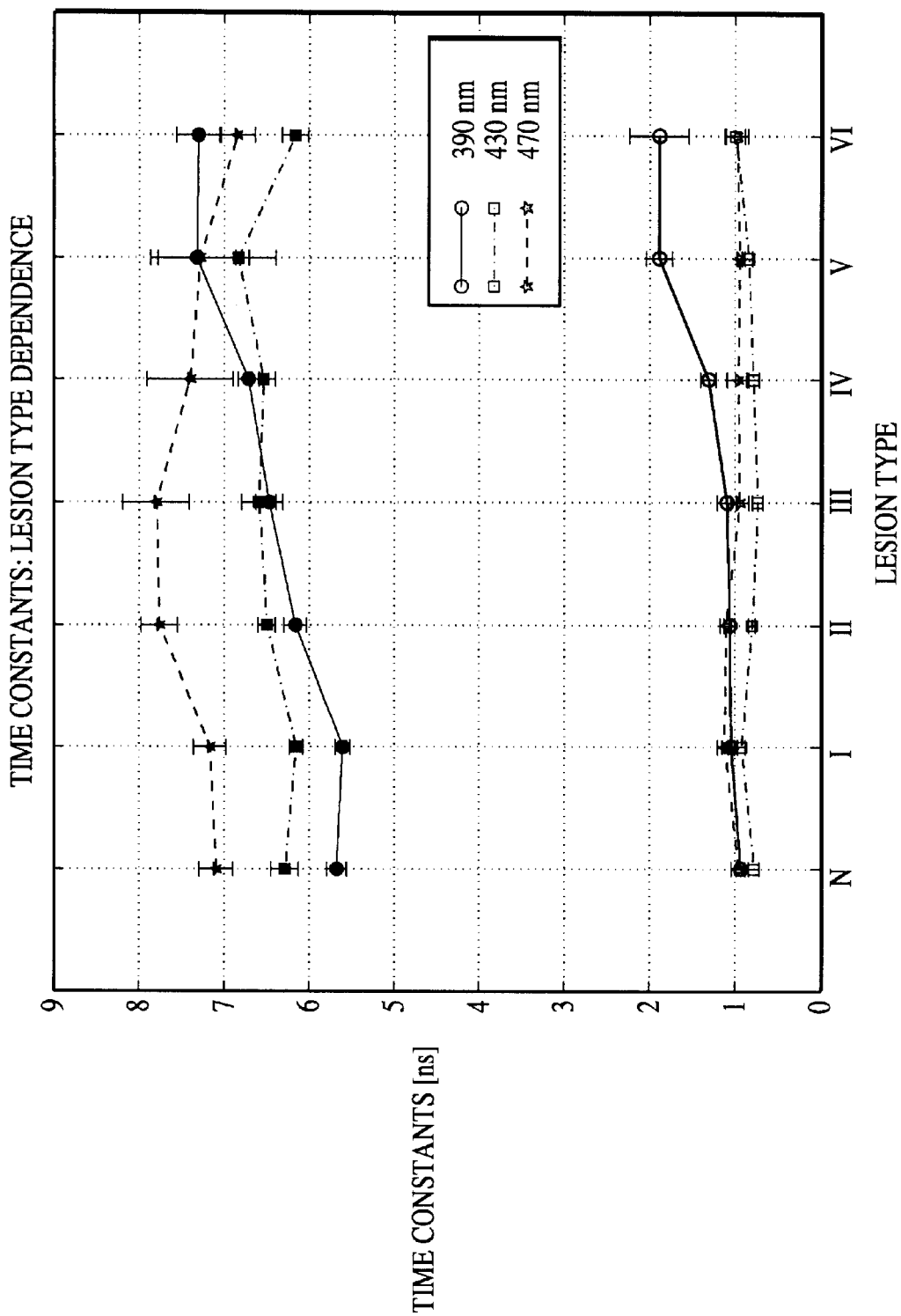
FIG. 10 are graphs showing: a) Variation (means +/−SE) of fast-term time constants, t1 (clear symbols), and slow-term time constant, t2 (fill symbols) at 390, 430, and 470 nm as a function of aortic lesion type; b) variation of fast-term amplitude contribution, A1 at 390, 430, and 470 nm as a function of aortic lesion type.
Figure 10B:
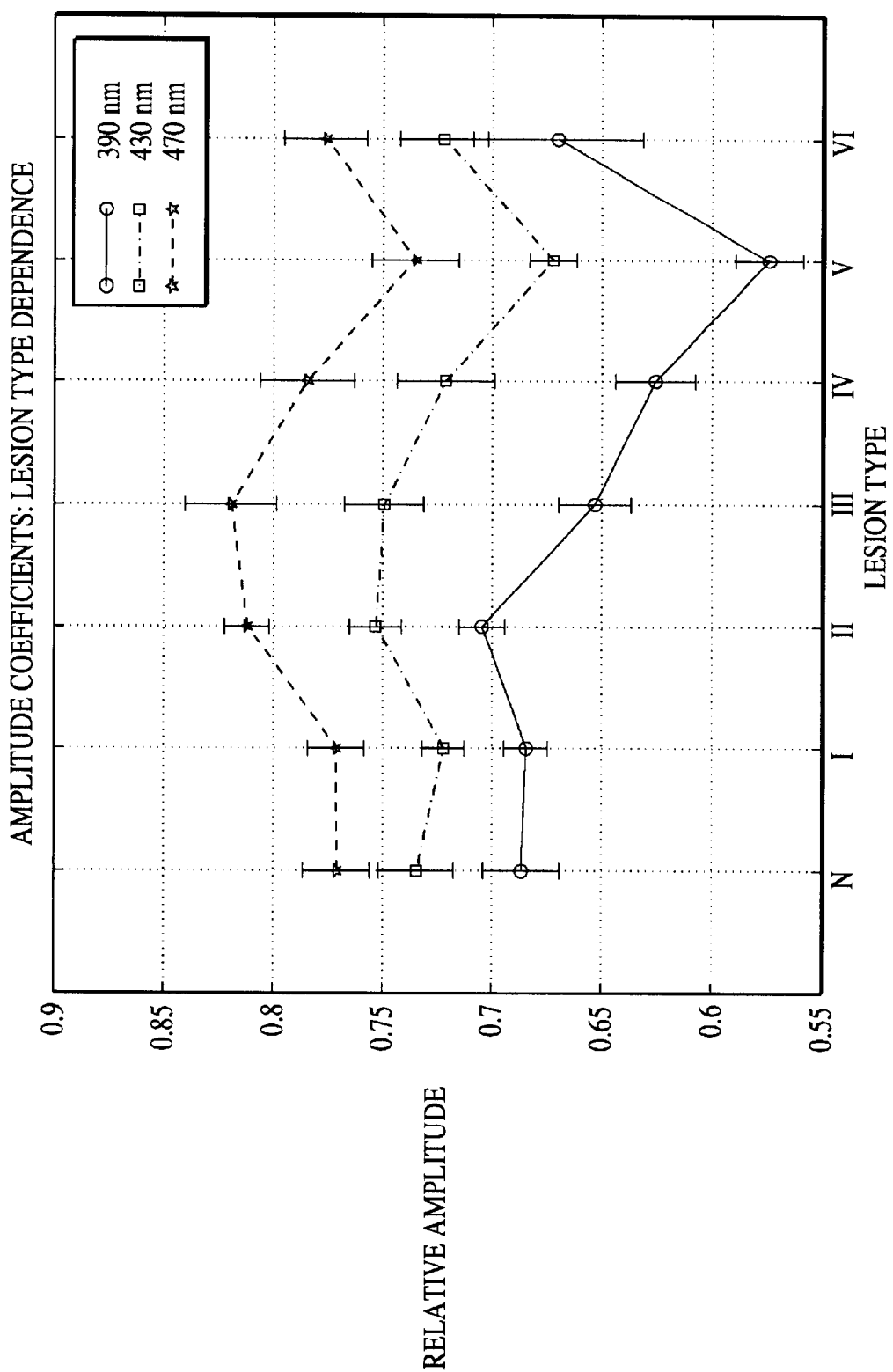

The variation of fluorescence decay characteristics as a function of lesion type is represented in FIG. 10 for 390, 430, and 470 nm emission. These wavelengths are representative of three spectral regions: 360–400 nm (region of main peak emission), 400–440 nm (middle spectral emission), 440–500 nm (region of second peak emission). The decay characteristics at 390 nm emission showed the highest variability as a function of lesion type. Both τ1 and τ2 significantly increased from normal to Type VI lesions, as shown in FIG. 10a. The increase of time constants was associated with a decreased contribution of fast-term time constant A1, see FIG. 10b, except for Type II and VI lesions. The decay constants at 430 and 470 nm emission exhibited less variability as a function of lesion type. However significantly increased A1 values at 470 nm emission were observed for all lesions type and particularly for Type II+III lesion (>0.8). These trends suggest that at longer wavelengths (e.g., 470 nm) the fluorescence emission is dominated by one decay component (emphasized for early (Type II) and more advanced (Type III) lesions). Type VI lesion showed decay time constants similar to those observed for Type V lesion but a significantly increased values for A1, suggesting a faster decay for calcified lesions.

Table 4 summarizes which of the decay constants (τ1, τ2, and A1) for 390 nm emission and fluorescence intensity at 470 nm (I470) are able to discriminate (post-hoc test, P<0.01) either between all types of lesion or between normal and each lesion type. Note 470 nm emission was chosen based on the observations of fluorescence emission in 470–490 nm range. The emission at this particular range appeared to better characterize the lipid rich lesions.

4. Classification of Aortic Lesions

Figure 11:
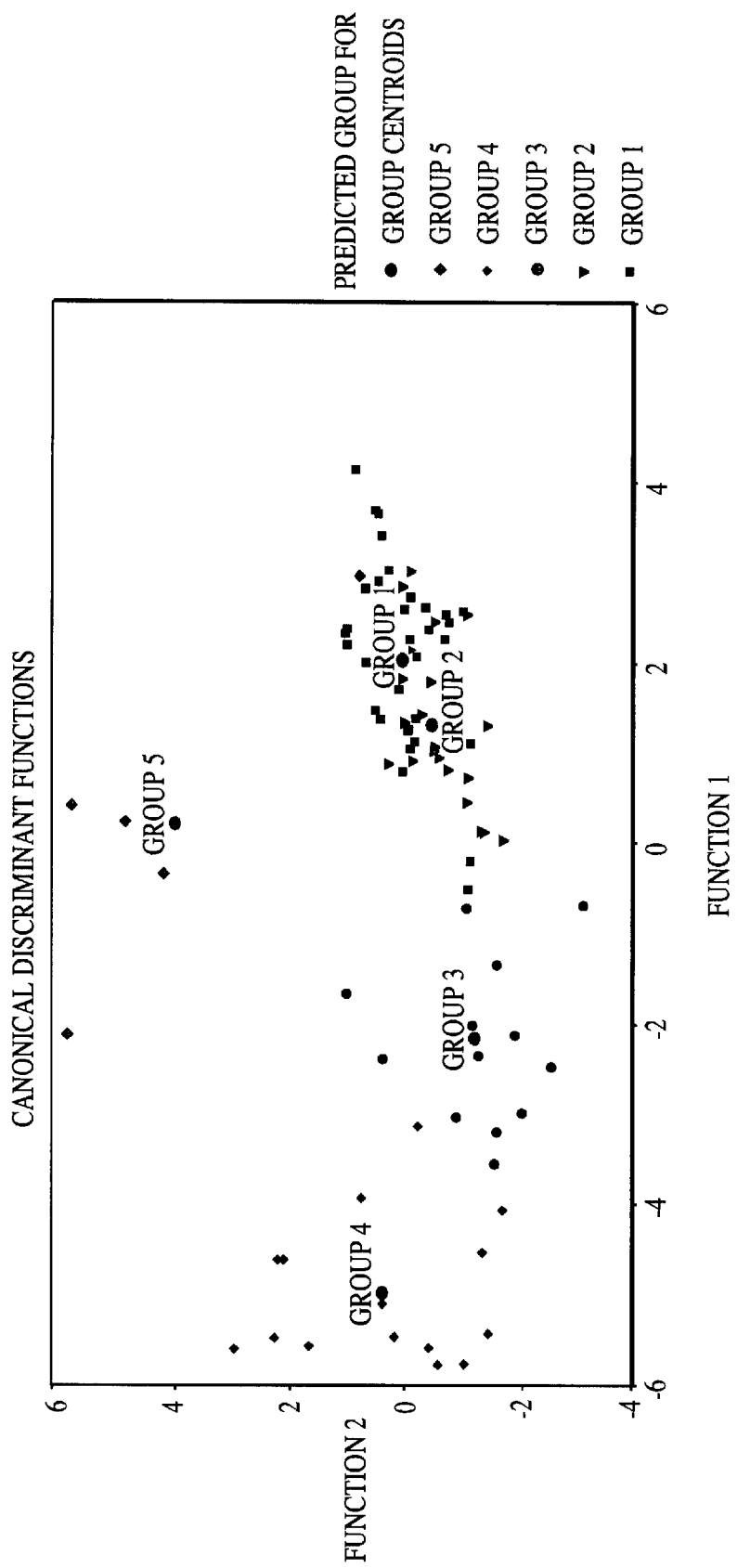
FIG. 11 is a two-dimensional scattered plot of the first and second discriminant functions determined based on the selected predictor variables (t1,t2, and A1 at 390 nm, t1 at 460 nm, and I490 nm)
Figure 12A:
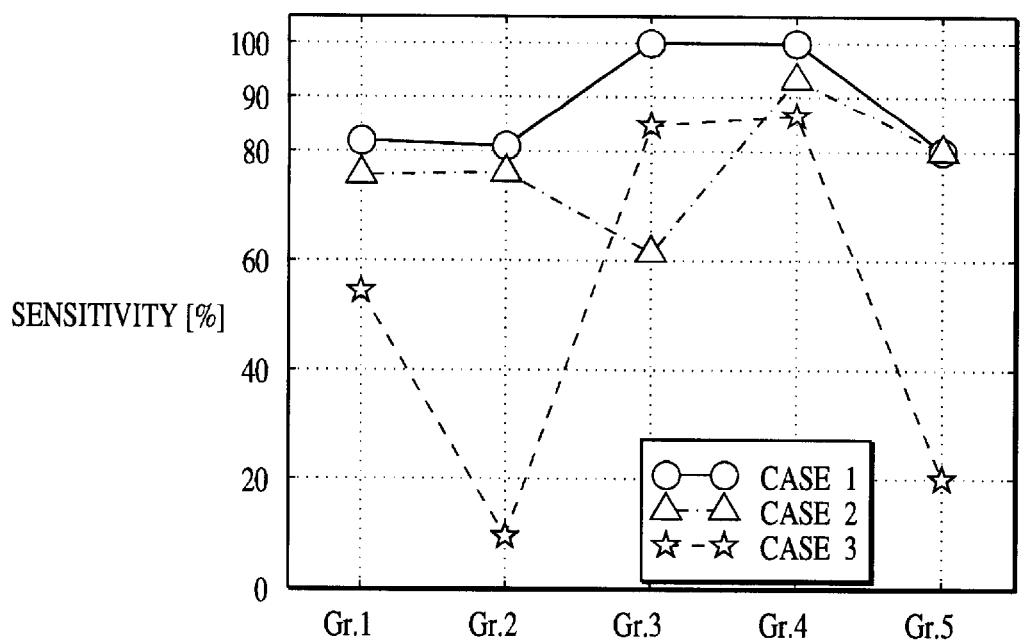
FIG. 12 show the classification (5 groups: Group 1 to 5) accuracy parameters (cross-validated set) for the three sets of possible predictor variables (Set 1: case 1; Set 2: case 2; Set 3, case 3). a) Sensibility; b) Specificity; c) Positive predictive values; d) Negative predictive values.
Figure 12B:
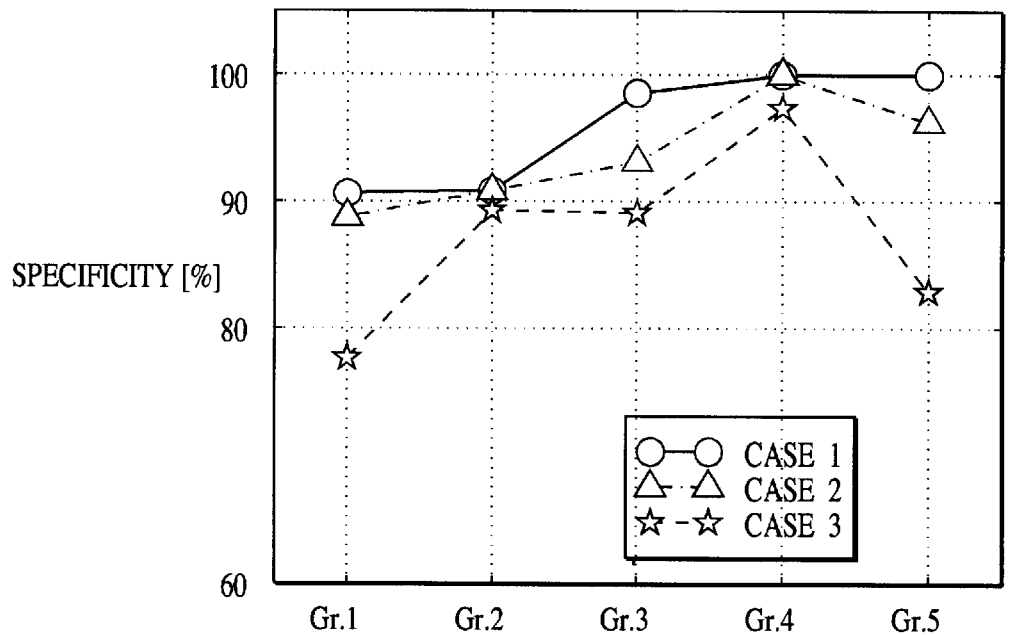
Figure 12C:
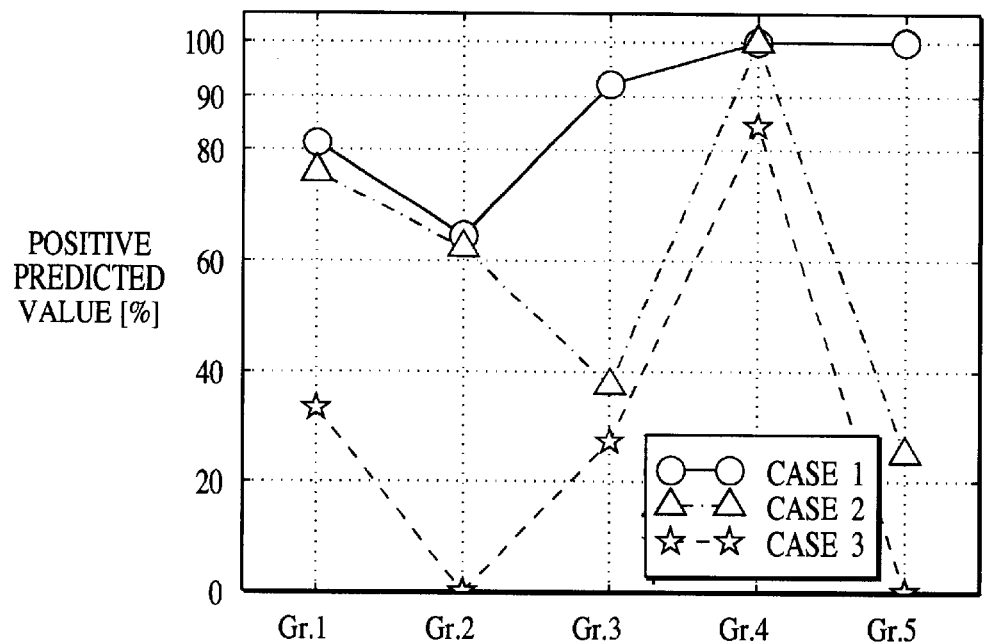
Figure 12D:
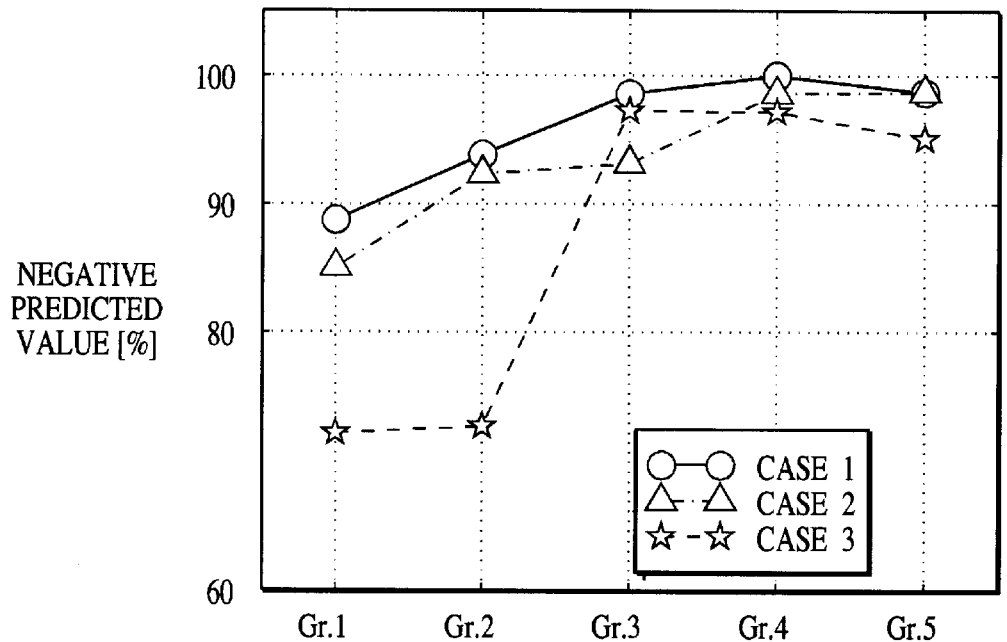
Figure 13A:
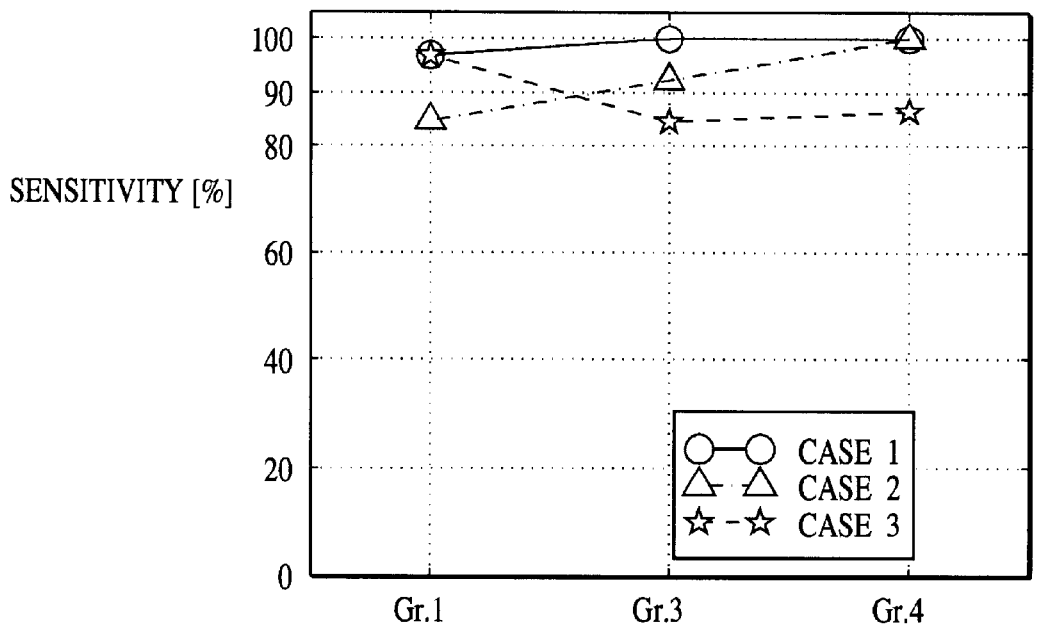
FIG. 13 displays the classification (3 groups: Groups 1, 3, and 4) accuracy parameters (cross-validated set) for the three sets of possible predictor variables (Set 1: case 1; Set 2: case 2; Set 3, case 3). a) Sensibility; b) Specificity; c) Positive predictive values; d) Negative predictive values.
Figure 13B:
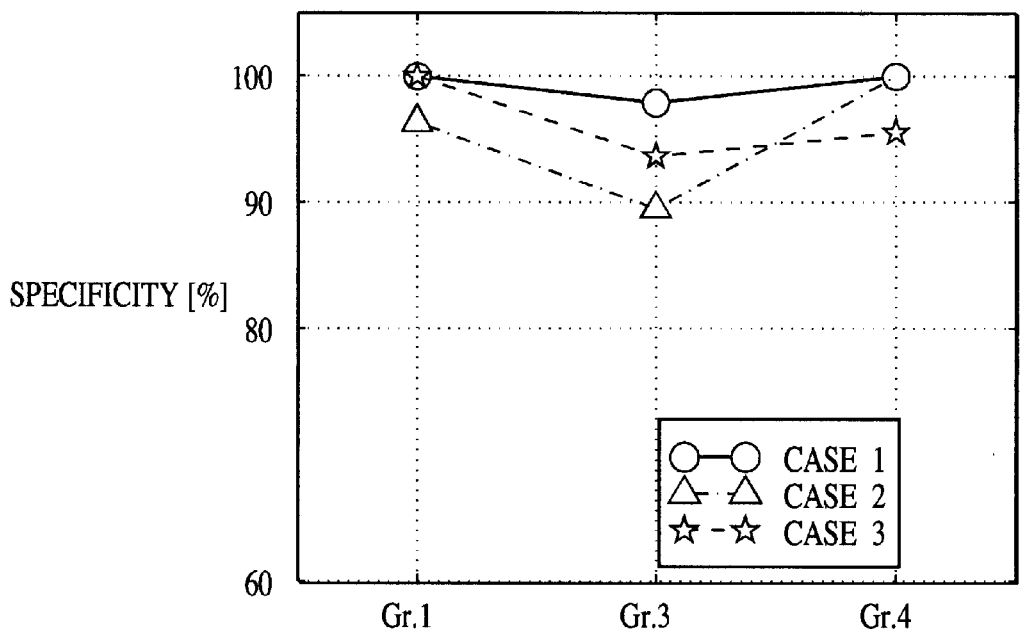
Figure 13C:
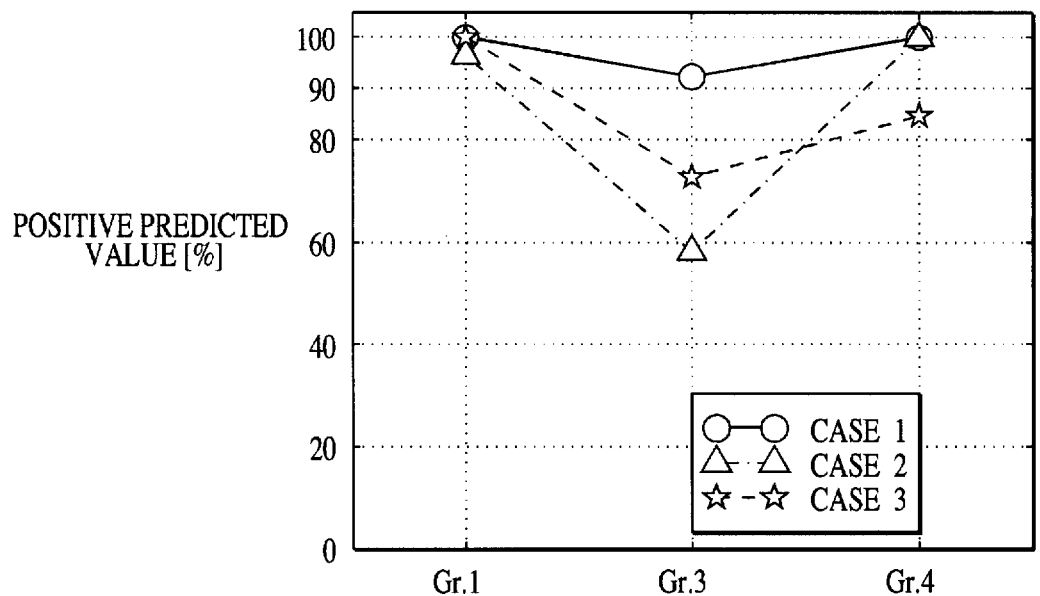
Figure 13D:
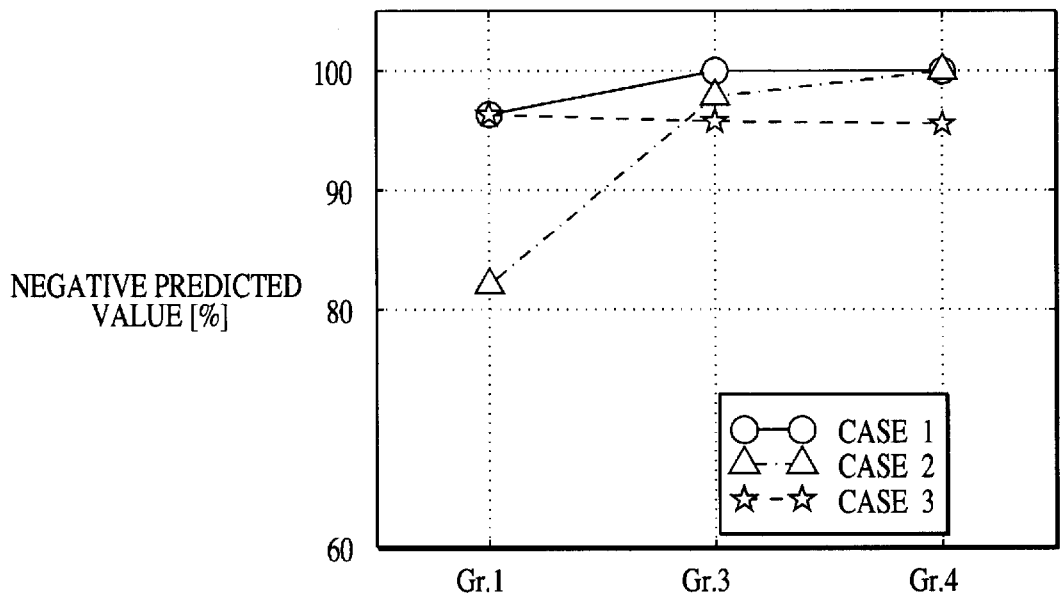

Using, the first set (Set 1) of possible predictor variables, the stepwise discriminant analysis algorithm applied on the training set selected five variables as predictor variables: τ1,τ2, and A1 at 390 nm, τ1 at 460 nm, and I490 in and generated four canonical discriminant functions. The territorial map shown in FIG. 11 of the first against the second discriminant function (Note: functions 1 and 2 account for 93.13% of the variance) indicates the directions along which the major differences between groups occur and reflect approximately how many cases are misclassified. The discriminant functions centroids shows that the first function discriminant direction clearly separates Groups 2, 3 and 4 in nearly equal steps, but shows a much less discrimination between Groups 1, 2, and 5. In terms of the second function direction, Group 5 is well distinguished from all other groups. Groups 1 and 2 shows the largest overlap in both directions.

Tables 5 and 6 depict the lesion classification in five groups based upon Set 1 of possible predictor variables (case 1) and the classification accuracy for training (T) and cross-validated (CV) sets. For training set, 28 (out of 33) from Group 1 and 17 (out of 21) from Group 2 specimens were correctly classified (sensitivity 84.8%, specificity 90.7% and sensitivity 80.9%, specificity 93.9% respectively). As expected from the large overlap between Group 1 and 2 observed on the territorial map of the discriminant functions (FIG. 11), the misclassified specimens from Group 1(4 specimens) were assigned to Group 2 and vice-versa, thus yielding a sensitivity of only 84.8% (specificity of 90.7%) and a sensitivity of 80.9% (specificity 93.9%) respectively. All specimens from Groups 3 and 4 were precisely classified (100% sensibility; 98.6% and 100% specificity respectively). Four out of five specimens from Group 5 were properly classified.

TABLE 5

Lesion Classification

| Total/ group | Predicted group membership | | | | | | | | | |
|---|---|---|---|---|---|---|---|---|---|---|
| | Group 1 | | Group 2 | | Group 3 | | Group 4 | | Group 5 | |
| | T | CV | T | CV | T | CV | T | CV | T | CV |
| Gr. 1 = 33 | 28 | 27 | 4 | 5 | 1 | 1 | — | — | — | — |
| Gr. 2 = 21 | 4 | 4 | 17 | 17 | — | — | — | — | — | — |
| Gr. 3 = 13 | — | — | — | — | 13 | 13 | — | — | — | — |
| Gr. 4 = 15 | — | — | — | — | — | — | 15 | 15 | — | — |
| Gr. 5 = 5 | — | — | — | — | — | — | — | — | 4 | 4 | a) 88.51% of training grouped cases (T) correctly classified (total groups sensitivity)
b) 86.23% of cross-validated grouped cases (CV) correctly classified.(total groups sensitivity)

TABLE 4

Decay constants and emission intensity - discrimination ability

| | N | I | II | III | IV | V |
|---|---|---|---|---|---|---|
| I | I470 | | | | | |
| II | τ2,I470 | τ2 | | | | |
| III | τ1,τ2,I470 | τ2,I470 | A1,I470 | | | |
| IV | τ1,τ2,I470 | τ1,τ2,I470 | A1,I470 | I470 | | |
| V | τ1,τ2,A1,I470 | τ1,τ2,A1,I470 | τ1,τ2,A1,I470 | τ1,τ2,A1,I470 | τ1,τ2,A1 | |
| VI | τ1,,τ2 | τ1,τ2 | τ1,τ2 | τ1,I470 | I470 | A1,I470 |

TABLE 6

Classification accuracy

| Classification accuracy parameters | Group 1 | | Group 2 | | Group 3 | | Group 4 | | Group 5 | |
|---|---|---|---|---|---|---|---|---|---|---|
| | T | CV | T | CV | T | CV | T | CV | T | CV |
| Sensitivity [%] | 84.8 | 81.8 | 80.9 | 80.9 | 100 | 100 | 100 | 100 | 80 | 80 |
| Specificity [%] | 90.7 | 90.7 | 93.9 | 90.9 | 98.6 | 98.6 | 100 | 100 | 100 | 100 |
| Pos. predicted values [%] | 82.1 | 81.4 | 76.4 | 64.7 | 92.3 | 92.3 | 100 | 100 | 100 | 100 |
| Neg. predicted values [%] | 90.7 | 88.8 | 93.9 | 93.9 | 98.6 | 98.6 | 100 | 100 | 98.7 | 98.7 |

The spectroscopic based classification of the histological border classified specimens based upon the discriminant functions generated from the training set is summarized in Table 7:

TABLE 7

Classification for specimens with border histological classification

| Total | Predicted group membership | | | | |
|---|---|---|---|---|---|
| | Group 1 | Group 2 | Group 3 | Group 4 | Group 5 |
| Type I–II = 16 | 9 | 7 | — | — | — |
| Type II–III = 6 | — | 4 | 2 | — | — |
| Type III–IV = 3 | — | — | 2 | 1 | — |

Note: Group 1 (Normal + Type I)
Group 2 (Type II)
Group 3 (Type III + Type IV)
Group 4 (Type V)

When the second set (Set 2, only time domain information) of possible predictor variables was used as input for the stepwise discriminant analysis algorithm four variables were selected as predictor variables: τ1,τ2, and A1 at 390 nm, and τ1 at 430 nm. Also, four discriminant functions remained in the analysis. For the third set (Set 3, only spectral information), one predictor variable (one discriminant function) was selected, I440.

A comparison between the accuracy of classification (5 Groups) achieved using the three sets (Set 1: case 1; Set 2: case 2; Set 3: case 3) of possible predictor variables is shown in FIG. 12. All classification accuracy parameters values (sensibility, specificity, positive and negative predictive values) for Set 1 were noticeable higher relative to the values determined for Set 2 and Set 3. Particularly, Group 3 and Group 4 showed high level of classification accuracy (numerical values in Table 3 (CV)), thus suggesting a clear improvement of discrimination for Type III+IV (lipid rich lesions) and Type V (collagenous plaque) when both time and spectral information are used for the determination of discriminant functions. Classification performance for Set 2 were slightly below that of Set 1, except for Group 3 (sensitivity <75%). Generally, Set 3 of variables shows a lower ability of discrimination, and particularly for discrimination of Group 2 (sensitivity <20%).

When Group 2 and Group 5 were excluded from analysis as shown in FIG. 13, the classification accuracy clearly increased for all three cases. The total group sensitivity increased as follow: for Set 1 to 98.4% (88.51% for 5 groups classification), for Set 2 to 90.2% (77.0%), and for Set 3 to 91.8% (50.6%). Note that using only time domain variables (Case 2) for analysis leads to higher classification accuracy for Group 3 (sensitivity 92.3%) and Group 4 (sensitivity 100%) when compared to the accuracy achieved for using only spectral domain variables (Group 3: 84.6%; Group 4: 86.7%). In fact, as shown in FIG. 13a, using only time domain data for three of the first four groups yielded a classification as nearly accurate as using the combination of both spectral data and time decay data. Thus, is it possible to construct a classification method that analyzed the fluorescent tissue only in the time domain, to the exclusion of the spectral domain to obtain resoanbly accurate infromation about the condition of the tissue.

The variables selected (three groups discrimination) from each entire set of predictor variables were: τ1,τ2, and A1 at 390 nm, τ1 at 460 nm, I420, I440, and I510 for Set 1; τ1,τ2, and A1 at 390 nm, τ1 at 460 nm, and A1 at 470 nm for Set 2; I440 for Set 3.

5. Discussion a. Histopathology

The thickness of intima for the various type of aortic specimens ranged between ~80 mm for normal aorta to ~1500 mm for Type V lesions. In previous studies, it has been shown that the penetration depth of 337 nm radiation in normal aortic tissue is roughly 150–200 mm and slightly higher (200–250 mm) for fatty plaques. Consequently for our study, the fluorescence emission of specimens with intima thickness <200 mm (i.e., normal, Type I, and ~50% of Type II) is likely to originate not only from intima but also from internal elastic lamina and media since aortic media is rich in elastin fibres. On the contrary, the emission of specimens with very thick intima (Type V) is likely to come from the top collagenous layers rather than from the entire thickness. This is a important issue for artery fluorescence emission interpretation and for spectroscopic lesions classification since fluorescence emission reflects only the composition of a particular tissue volume and does not reflect the composition of intima itself or the entire intima depth respectively.

b. Spectro-temporal Fluorescence Emission of Aortic Lesions

Fluorescence emission of the atherosclerotic arterial samples (types I–VI lesions) showed significant differences in both spectral and temporal dimension. Also, the emission of the atherosclerotic lesions differed from that of the normal arterial tissue. In spectral dimension, the fluorescence lineshapes of normal aortic wall and of early lesions were distinctive from the lineshapes of more advanced lesions, although for all lesion types the main peak emission was centered at ~380 nm. Normal and less atherosclerotic tissue presented a broad spectral emission with a secondary peak at longer wavelengths (440–470 nm), whereas more advanced atherosclerotic specimens exhibited a low level of emission at wavelengths >420 nm. Generally, a gradual decrease of emission at longer wavelength occurred with increased atherosclerotic level. Spectral emission of Type VI lesion (calcified) was an exception from this rule. For lesions of Type VI the intensity emission at wavelengths >420 nm showed a large variability and the mean spectra resembled the emission of the early lesions rather the emission of advanced lesions. In time domain, the overall emission of normal aorta and early lesions was shorter (e.g., ~10 ns) and relatively constant over the investigated wavelength range. Whereas the emission of more advanced lesion i) was longer (gradually increased with increased atherosclerotic level Type III ~13 ns, Type V ~16 ns) and ii) exhibited a decrease as a function of wavelength (e.g., Type V, 390 nm: ~16 ns; 470 nm: ~13 ns). The emission of Type VI lesions lasted also longer (~13 ns), in the range of more advanced lesions emission. The spectral trends described in this study are in agreement with aortic spectra reported by previous studies, especially those that used for investigation excitation at 337 nm and 325 nm.

For the time domain, Baraga et al. and Andersson-Engels found fluorescence decay characteristics for arterial tissue, i.e., faster decay for normal (380 nm, ~6.03 ns) and longer for atherosclerotic (~7.33 ns) tissue, thus the results are also in agreement with these early studies. Nevertheless, no extensive conclusions can be obtained from this comparison since these studies investigated the temporal decay only for one or three wavelengths, employed different excitation wavelength and used picosecond laser pulses.

Elastin, a major component of internal elastic lamina and of aortic media, has been considered the dominant fluorophore for normal aorta, whereas collagen, a protein that accumulates during atherosclerotic process, has been evidenced as the main fluorophore for advance atherosclerotic plaque. Therefore, previous studies have attributed the fluorescence lineshapes difference between normal and graded levels of atherosclerosis primarily to the relative change of elastin/collagen content (decreased elastin/collagen concentration ratio from initial lesions to advanced lesions), although several additional other fluorophores (ceroid, cholesterol, LDL, tryptophan) were suggested as responsible for spectral variability. The results are in agreement with these early studies by showing a broad spectral emission (similar to elastin emission, not discussed here) for normal and initial lesions (Type I, II) and a narrow emission (similar to collagen emission, for advanced lesions (Type V). Additionally, we expand these similarities to the time domain spectra by determining a direct relationship between the FIRFs of pure components with those of arterial samples: a shorter emission decay (~10 ns) for normal and initial lesions (elastin (~13 ns), and a longer decay (~16 ns) for Type V lesions (collagen (~18 ns). Yet across the spectrum, the emission of normal and Type I lesions was relatively constant (similar to elastin), whereas for type V lesions emission decreased (similar to collagen).

For Type III and IV lesions (lipid lesions), a decrease of fluorescence intensity at longer wavelengths (spectral domain) and lengthening of emission (time domain) was observed. However, an increase of collagen amount is not a feature for these lesions and elastin fibers from lesions containing increasing amount of lipids are known to undergo modification of conformation and proteolytic degradation. Also, for most of Type III and some of Type IV lesions, an increase of intensity (spectral domain) in the 470–490 nm wavelength range and a delay of emission peak of 0.5 ns (time domain) was observed. Consequently, these emission characteristics can not be described only by change in elastin/collagen content. Early studies reported the fluorescence of peroxidized lipoproteins, LDL, free cholesterol, lipids contained in arterial wall. Also these studies suggested that the fluorescence characteristics of lipid rich lesions is a superposition of the emission of the dominant lipid component accumulated in tissue and the emission of structural proteins. In the above described lipid experimentation, the inventors of the subject invention presented the emission of free and esterified (cholesteryl oleate and linoleate) cholesterol, the major lipid components that accumulate during atherosclerotic process. For these lipids a 0.5 ns emission delay in 470–490 nm wavelength range was determined. The present results are in agreement with those previously reported. Additionally, there are clear similarities between spectro-temporal emission of lipid plaques and that of pure lipid components of plaque lipid-rich core. Although the temporal resolution of our experimental setup did not allow a better characterization of the emission, our findings suggest that the time domain emission in 470–490 nm range could provide additional information for composition characterization and detection of atherosclerotic plaque.

The emission of Type VI lesions presented a large variability in spectral domain (I470 nm=%) and their lineshapes were practically undistinguished from those of normal and initial lesions. Previous studies have shown that the absorption spectra of calcified plaques varies more than the absorption spectra of other type of plaques and attributed this trend to a grater diversity in the composition of calcified lesions compared to lipid or fibrous lesions. Also, it was noted that studies that used excitation at 337 nm, and 325 nm have not proven a capability of diagnostic for calcified plaque (spectra similar to normal aorta). In time domain, it was observed that calcified lesion emission was fairly constant (~13 ns) for all specimens and resembled the decay of more advanced lesion rather than normal arterial wall, thus suggesting that analysis of time-resolved spectra can complement the spectral emission for discrimination of calcified plaques at 337 nm excitation.

c. Decay Characteristics of Aortic Lesions

The decay constants ($\tau 1$, $\tau 2$, A1) retrieved by biexponential approximation of FIRF offered a complementary mean for fluorescence emission decay characterization. Their variation as function of wavelength indicate that the decay constants obtained for 370–410 nm wavelength range vary the most as a function of lesion type, thus suggesting that emission in this wavelength range is more likely to differentiate between different levels of atherosclerosis. Also for early lipid lesions (Type II) and more advanced Type III, the increased contribution of slow-term amplitude A1 (especially at longer wavelengths 470–490 nm) evidence an enhanced contribution from a component with fast emission decay. Fluorescence emission of cholesteryl oleate, primarily lipid found in foam cells (characteristics of Type II lesions), was previously found to exhibit a shorter emission (~9 ns). Therefore, the results suggest that fluorescence of cholesteryl oleate could be reflected on the emission of early lipid lesions.

6. Classification of Aortic Lesions

The present study examined the ability of various groups of predictor variables derived from the spectro-temporal fluorescent emission characteristics of the aortic wall to discriminate between atherosclerotic lesions. Five predictor variables (four derived from time domain, $\tau 1$, $\tau 2$, A1 at 390 nm and $\tau 1$ at 460 nm, and one from spectral domain, I490) were found by a linear discriminant analysis algorithm to best separate five groups of specimens: Normal+Type I, Type II (fatty-streaks), Type III+Type IV (lipid lesions: preatheroma+atheroma), Type V (collagenous fibrous lesions), and Type VI (calcified lesions). This grouping was meant to mimic as close as possible the AHA classification, a histological classification of human atherosclerotic lesions that reflect both their composition and structure and the temporal natural history of the disease. A high classification accuracy was obtained (cross-validated set) for Group 3(III+ IV) and Group 4 (V), i.e., with 100% sensitivity and >98% specificity. The potential clinical significance of the accurate discrimination of Type III and, especially, of Type IV could be very important since the region between the lipid core and the lesion surface (contains proteoglycans and macrophage foam cell and only isolated smooth muscle cells and minimal collagen) is susceptible to fissures formation and the periphery of advanced Type IV lesions could be vulnerable to rupture. A relatively lower accuracy was achieved for Group 1 (normal+Type I) and Group 2 (Type II), i.e., >80% sensitivity and >90% specificity. However, this result was anticipated since ~50% of type II lesions had a thin intimal thickness <200 mm (in the range of normal and Type I lesions), thus the fluorescence originated from elastin media is likely to be superimposed on their overall emission, whereas more advanced lesion groups (thickness >300 mm) are more likely to originate their fluorescence emission from only intimal components. Only 5 specimens were available from Group 5 (Type VI), thus no extensive conclusions can be drawn. Yet, 4 out of 5 specimens were correctly classified (100% positive predictive value), and a clear differentiation from Type V and IV lesions was acquired for calcified lesions (one classified as Group 1). Thus time-resolved information facilitated the discrimination of calcified lesions excited with 337 nm. Overall, a sensitivity >86% was obtained. The relatively low value for sensitivity was due mainly due to the poor classification of Group 2 (Type II). Excluding, Group 2 and Group 5 from analysis, a sensitivity of >98% was achieved. Using predictor variables from only spectral domain or from only time domain in the analysis, decreased the accuracy of classification for all five groups. These results suggest that using predictors variables from both spectral and time domain, the classification accuracy could be noticeable increased. Besides, the result of classification for the specimens with border histological classification indicates for all specimens a predicted group membership that concord with the transient histopathological type from which they originate.

Previous studies have used for classification primarily binary algorithms based exclusively on spectral information. The performance review for various classifiers reported by others showed that principal component analysis and stepwise multivariate linear regression performed best (overall 96% accuracy) when used for the classification (normal/ advanced atherosclerotic) of aortic specimens excited with HeCd laser (325 nm) in air. To our knowledge only one study by Morguet et al., tried to classify more than 2 or 3 types or spectra. Using XeCl laser (308 nm) for excitation (in saline and blood) of aortic specimens and an linear discriminant analysis algorithm (predictor variables: two intensity ratios) they have shown that five types of spectra can be differentiated with ongoing ablation (media, atheromas, fibrous plaque (all three in saline and blood), calcified in saline, and calcified in blood) with an overall sensitivity 93.2%. Also, they reported that lipid plaque (Type III+IV) could be differentiated from fibrous plaque (Type V) with a sensitivity >83% (sensibility >96%). The present study shows that using both spectral and time-resolved information lead to increased accuracy of classification for Type III+IV lesions and Type V (sensitivity 100%, specificity >98%). No extensive comparison can be made between the subject study (5 spectral groups) with the Morguet et al. study (5 spectral types), since different experimental conditions were used for spectra acquisition (wavelength, blood, saline, ongoing ablation) and different type of aortic tissue were compared. However excluding from analysis Type II (not investigated by previous study) and Type V (spectral emission for calcified lesion can not be well differentiated with 337 nm excitation), the results shows that the classification accuracy based upon only spectral information (>91.8%) is comparable to that reported by Morguet et al.(>93.2%). When, adding the time-resolved information, the accuracy for three groups classification increased to >98.6% due to increase accuracy for Type III+IV and Type V, thus suggesting that 1) emission decay is an important predictor for lipid rich lesions 2) time-resolved emission information improves the classification accuracy.

The inventors observed that various sets of time and/or spectral domain parameters were selected as important predictor variables by linear discriminant analysis algorithm. Overall for all cases the decay constants derived from 390 nm ($\tau 1, \tau 2, A1$), 430 nm ($\tau 1$), and 460 nm ($\tau 1$) emission and fluorescence intensities at 440 and 490 nm were chosen for discrimination. These results suggest that variables from only a few wavelengths are able to discriminate between different levels of atherosclerosis, thus the emission at a few proper selected wavelengths can be used for diagnostic based on time-resolved spectroscopy. The linear discriminant analysis consistently selected the decay constants at 390 nm emission as predictor variables. This variables selection is in agreement with the significant variation of decay constants at 390 nm as a function of lesion type and indicates time-resolved emission at one wavelength from main peak wavelength band as an important predictor variables for lesion discrimination. Based on univariate analysis, for the wavelengths band >420 nm, it was noted that the variables that account for most of the differences among lesion types were derived from spectral domain rather than time domain, although particular time-resolved features of lipid rich lesions were observed for 470–490 nm range. The discriminant analysis algorithm selected for discrimination variables that appertain to both domains ($\tau 1$ at 460 nm and I490). Also, for the different classification cases investigated, we observed that the predictor variables selected for some case were replaced by different variables (e.g., $\tau 1$ at 430 nm and I440) for other cases. It will be appreciated that these results suggest that at the longer wavelengths the discriminant analysis method failed to identify a consistent set of predictor variables. It appears that the genuine features of each group are diluted over the number of input predictor variables, therefore particular biased features are allowed to prevail. Previous studies had documented that linear discriminant models tends to become overfit very quickly as more variables were added. Also, it has been suggested that a rational elimination of variables which are obviously useless or replacing the predictor variables set with their principal components scores set could give a much more robust solution to the discriminant analysis method. Consequently for the subject study, using a set of a few predictor variables derived from a detailed examination of univariate analysis results could lead to a better classification of arterial samples. A secondary approach is to use a principal component analysis as a data reduction technique. This could allow full time-resolved spectra coverage for all samples and mitigate the need for wavelength selection. Nevertheless the present findings suggest that variables from emission at a few (5–6) discrete wavelengths in 420–510 nm range can complement those determined from peak emission for an accurate lesion classification.

The present study demonstrates that time-resolved fluorescence emission data tends to significantly improve the spectroscopic classification of aortic samples in-situ and suggests that time resolved information can complement spectral information for a better characterization of atherosclerotic lesions during surgical procedures. The distinct characteristics and the high accuracy of classification determined for lipid-rich lesions evidenced the potential of this technique for clinical diagnostic of lesions prone to rupture.

Having thus described exemplary embodiments of the invention, it is understood that the forgoing discussion, which focused on the particular example of analysis of the arterial wall for atherosclerosis, the present methodology could be equally applied to other organic matter and, in particular, other human tissue such as a tumorous masses or blood plasma, that can be classified by its intrinsic fluorophores, according to its stage of development, deterioration or disease.

It will be further apparent that alterations, modifications, and improvements will also occur to those skilled in the art. For example, it will be apparent that the instrumentation of the present invention is not limited to use in research facilities and in a catheter-based apparatus. It is also contemplated that the above-described methods may be implemented in other instruments not expressly described. Several nonlimiting examples include a table top, time-resolved laser spectroscopy systems with self-contained processing power for use in a lab, or hand-held lipid profiling readers connected to the processing units for remote user or direct use in the field. Such alterations, modifications, and improvements, though not expressly described or mentioned above, are nonetheless intended and implied to be within the spirit and scope of the invention. Accordingly, the foregoing discussion is intended to be illustrative only; the invention is limited and defined only by the various following claims and equivalents thereto.

We claim:

1. A method of identifying the histological condition of tissue by analyzing protein and lipid components in the tissue, comprising:
   (a) exciting the tissue with ultraviolet laser light of a suitable excitation wavelength and excitation intensity to cause the tissue to reemit light;
   (b) resolving the reemitted light into component wavelengths within a predetermined bandwidth;
   (c) determining the time-resolved emission of the reemitted light at one or more of the component wavelengths;
   (d) obtaining spectral intensity data representative of the intensity of the reemitted light at the one or more component wavelengths;
   (e) obtaining intensity decay data representative of the time-resolved emission of the reemitted light at the one or more component wavelengths; and
   (f) processing the spectral intensity data and intensity decay data in order to analyze the histological condition of the tissue.

2. The method of claim 1, wherein the determining the time-resolved emission includes applying an appropriate deconvolution algorithm to obtain the fluorescent impulse response function (FIRF) of the reemitted light at the one or more component wavelengths.

3. The method of claim 2, wherein the processing further comprises comparing the spectral intensity data and intensity decay data to preclassified data representative of a tissue classification system in order to characterize the tissue.

4. The method of claim 3, wherein the tissue is a portion of an arterial wall and the processing further includes:

discriminating between graded levels of atherosclerotic lesions and classifying the portion of the arterial wall based upon the preclassified data representative of the tissue classification system.

5. The method of claim 4, wherein the excitation wavelength of the ultraviolet laser light is approximately 337 nanometers.

6. The method of claim 3, wherein the tissue is a tumorous mass.

7. The method of claim 3, wherein the tissue is blood plasma.

8. The method of claim 1, wherein the tissue is situated in vivo.

9. The method of claim 1, further including:
   exciting the tissue with ultraviolet laser light at a suitable excitation wavelength that is different from the previous excitation wavelength to cause the tissue to reemit light; and
   repeating (b), (c), (d), (e) and (f) to further analyze the histological condition of the tissue.

10. A method of identifying the histological condition of tissue by analyzing protein and lipid components in the tissue, comprising:
    (a) exciting the tissue with ultraviolet laser light of a suitable excitation wavelength and excitation intensity to cause the tissue to reemit light;
    (b) resolving the reemitted light into component wavelengths within a predetermined bandwidth;
    (c) determining the time-resolved emission of the reemitted light at one or more of the component wavelengths;
    (d) obtaining intensity decay data representative of the time-resolved emission of the reemitted light at the one or more component wavelengths; and
    (e) processing the intensity decay data in order to analyze the histological condition of the tissue.

11. A method of identifying the presence or absence of a protein or lipid in tissue, comprising:
    (a) exciting the tissue with ultraviolet laser light of a suitable excitation wavelength and excitation intensity to cause the tissue to reemit light;
    (b) resolving the reemitted light into component wavelengths within a predetermined bandwidth;
    (c) determining the time-resolved emission of the reemitted light at one or more of the component wavelengths;
    (d) obtaining intensity decay data representative of the time-resolved emission of the reemitted light at the one or more component wavelengths; and
    (e) processing the data and comparing the data to reclassified data representative of the fluorescence of relatively pure protein and lipid components in order to analyze the histological condition of the tissue.

12. A system for identifying the histological condition of tissue by analyzing protein and lipid components in the tissue, comprising:
    an ultraviolet laser excitation source that produces a light beam of a predetermined wavelength, intensity and pulse rate;
    an ultraviolet laser delivery and collection mechanism that transmits the excitation light beam from the source to the tissue;
    a light dispersing subsystem that resolves the reemitted light into component wavelengths within a predetermined wavelength range;

a detector that detects the resolved light and converts it into an electrical signal;

a converter that digitizes the electrical signal; and a processor that substantially automatically processes the digitized signal to provide data indicative of the histological condition of tissue.

13. The system of claim 12, wherein the processor deconvolves the digitized signal to obtain an impulse response function, approximates the deconvolved data with an appropriate approximation function and applies the approximated data to a classification system to classify the histological condition of the tissue.

14. The system of claim 12 wherein the ultraviolet laser delivery and collection mechanism is contained in a probe.

15. The system of claim 14, wherein the probe is a catheter.

16. The method of claim 4, wherein the discriminating includes discriminating lipid-rich lesions in the tissue from non-lipid-rich lesions.

17. A method of identifying lipid-rich lesions in arterial wall tissue, comprising:

(a) exciting the tissue with ultraviolet laser light of a suitable excitation wavelength and excitation intensity to cause the tissue to reemit light;

(b) resolving the reemitted light into component wavelengths within a predetermined bandwidth;

(c) determining the time-resolved emission of the reemitted light at one or more of the component wavelengths;

(d) obtaining intensity decay data representative of the time-resolved emissions of the reemitted light at the one or more component wavelengths;

(e) processing the intensity decay data in order to identify the lipid-rich lesions in the tissue.

* * * * *